United States Patent
Yoshinaga et al.

(10) Patent No.: US 10,130,563 B2
(45) Date of Patent: Nov. 20, 2018

(54) DENTAL POLYMERIZABLE MONOMER COMPOSITIONS

(71) Applicants: MITSUI CHEMICALS, INC., Minato-ku, Tokyo (JP); SHOFU INC., Kyoto-shi, Kyoto (JP); SUN MEDICAL CO., LTD., Moriyama-shi, Shiga (JP)

(72) Inventors: Kazuhiko Yoshinaga, Ichihara (JP); Hiroshi Naruse, Chiba (JP); Mitsuji Teramae, Kyoto (JP); Kiyomi Fuchigami, Kyoto (JP); Hidefumi Fujimura, Kyoto (JP); Masuji Tsuchikawa, Moriyama (JP); Hirofumi Imai, Moriyama (JP)

(73) Assignees: MITSUI CHEMICALS, INC., Minato-Ku, Tokyo (JP); SHOFU INC., Kyoto-Shi, Kyoto (JP); SUN MEDICAL CO., LTD., Moriyama-Shi, Shiga (JP)

( * ) Notice: Subject to any disclaimer, the term of this patent is extended or adjusted under 35 U.S.C. 154(b) by 113 days.

(21) Appl. No.: 15/300,669

(22) PCT Filed: Mar. 31, 2015

(86) PCT No.: PCT/JP2015/060083
§ 371 (c)(1),
(2) Date: Sep. 29, 2016

(87) PCT Pub. No.: WO2015/152220
PCT Pub. Date: Oct. 8, 2015

(65) Prior Publication Data
US 2017/0181932 A1 Jun. 29, 2017

(30) Foreign Application Priority Data

Mar. 31, 2014 (JP) ................................. 2014-072635
Mar. 31, 2014 (JP) ................................. 2014-072636

(51) Int. Cl.
*A61K 6/083* (2006.01)
*A61K 6/00* (2006.01)
*C07C 271/20* (2006.01)

(52) U.S. Cl.
CPC ............ *A61K 6/083* (2013.01); *A61K 6/0023* (2013.01); *A61K 6/0073* (2013.01); *A61K 6/0097* (2013.01); *A61K 6/0835* (2013.01); *C07C 271/20* (2013.01); *C07C 2102/42* (2013.01)

(58) Field of Classification Search
None
See application file for complete search history.

(56) References Cited

U.S. PATENT DOCUMENTS

| 4,345,058 A | * | 8/1982 | Dettling | C08G 18/4854 |
| | | | | 12/147 A |
| 4,567,237 A | * | 1/1986 | Johnson | C08F 299/026 |
| | | | | 525/111 |
| 5,763,622 A | * | 6/1998 | Podszun | A61K 6/0017 |
| | | | | 430/302 |
| 5,849,270 A | * | 12/1998 | Podszun | A61K 6/0023 |
| | | | | 424/55 |
| 6,037,014 A | * | 3/2000 | Edgington | C08F 299/02 |
| | | | | 427/388.1 |
| 2002/0082315 A1 | | 6/2002 | Moszner et al. | |
| 2006/0257782 A1 | | 11/2006 | Maemoto | |
| 2009/0054543 A1 | * | 2/2009 | Nozawa | C07C 265/12 |
| | | | | 522/73 |
| 2012/0129973 A1 | | 5/2012 | Sun | |

(Continued)

FOREIGN PATENT DOCUMENTS

JP 6-009919 A 1/1994
JP 6-172686 A 6/1994

(Continued)

OTHER PUBLICATIONS

International Search Report (PCT/ISA/210) dated Jun. 30, 2015, by the Japanese Patent Office as the International Searching Authority for International Application No. PCT/JP2015/060083.

(Continued)

*Primary Examiner* — Peter A Salamon
(74) *Attorney, Agent, or Firm* — Buchanan, Ingersoll & Rooney PC

(57) ABSTRACT

Provided are dental polymerizable monomer compositions that can give cured products having high toughness and high rigidity, and dental compositions containing such dental polymerizable monomer compositions and cured products thereof having high mechanical properties. The dental polymerizable monomer composition includes a urethane acrylate compound (A) and a polymerizable compound (B) having at least one polymerizable group selected from methacryloyl groups and acryloyl groups, the urethane acrylate compound (A) being obtained by reacting a specific hydroxyacrylate (a1) with a diisocyanate (a2) having two isocyanate groups bonded to a divalent $C_{6-9}$ aromatic hydrocarbon group or a divalent $C_{6-9}$ bridged cyclic hydrocarbon group via a methylene group optionally substituted with a hydrocarbon group in place of a hydrogen atom, the proportion of the number of acryloyl groups present in the urethane acrylate compound (A) being 10% to less than 90% relative to the total number of (meth)acryloyl groups in the monomer composition.

12 Claims, No Drawings

(56) References Cited

U.S. PATENT DOCUMENTS

| | | | |
|---|---|---|---|
| 2012/0296003 A1 | 11/2012 | Naruse et al. | |
| 2012/0296061 A1 | 11/2012 | Naruse et al. | |
| 2013/0103157 A1* | 4/2013 | Kourtis | A61F 2/30 623/18.11 |
| 2017/0327624 A1* | 11/2017 | Kourtis | C08G 18/6229 |

FOREIGN PATENT DOCUMENTS

| | | |
|---|---|---|
| JP | 9-176151 A | 7/1997 |
| JP | 9-216924 A | 8/1997 |
| JP | 11-315059 A | 11/1999 |
| JP | 2000-204069 A | 7/2000 |
| JP | 2005-053898 A | 3/2005 |
| JP | 2006-276274 A | 10/2006 |
| JP | 2013-544823 A | 12/2013 |
| WO | WO 2012/071329 A1 | 5/2012 |
| WO | WO 2012/157566 A1 | 11/2012 |

OTHER PUBLICATIONS

Written Opinion (PCT/ISA/237) dated Jun. 30, 2015, by the Japanese Patent Office as the International Searching Authority for International Application No. PCT/JP2015/060083.

International Search Report (PCT/ISA/210) dated Jun. 30, 2015, by the Japanese Patent Office as the International Searching Authority for International Application No. PCT/JP2015/060084.

Written Opinion (PCT/ISA/237) dated Jun. 30, 2015, by the Japanese Patent Office as the International Searching Authority for International Application No. PCT/JP2015/060084.

\* cited by examiner

DENTAL POLYMERIZABLE MONOMER COMPOSITIONS

TECHNICAL FIELD

The present invention relates to novel dental polymerizable monomer compositions, dental compositions including the polymerizable monomer compositions, and cured products obtained by curing the dental compositions.

BACKGROUND ART

Composite resins that are a typical example of dental compositions usually contain a polymerizable monomer composition and additives such as a filler, a polymerization initiator, a polymerization inhibitor, a dye, and etc. In a composite resin including such components, a filler usually has the largest weight fraction followed by a polymerizable monomer composition and these two components represent a major proportion of the weight of the composite resin. The polymerizable monomer composition serves as a binder for the filler. The properties of monomers, and the properties of cured products of the compositions are significantly influential on the properties and performance of the composite resin containing the monomer composition, and cured products thereof.

From the points of view of aspects such as the biological safety of monomers and the mechanical strength and wear resistance of cured products, the polymerizable monomer compositions frequently include radically polymerizable polyfunctional methacrylates. Typically, the polyfunctional methacrylate compositions are based on 2,2-bis[4-(3-methacryloyloxy-2-hydroxypropoxy)phenyl]propane (hereinafter, written as Bis-GMA) or 2,2,4-trimethylhexamethylenebis(2-carbamoyloxyethyl) dimethacrylate (hereinafter, written as UDMA), and contain triethylene glycol dimethacrylate (hereinafter, written as TEGDMA) to control the viscosity.

In the dental clinical practice, the use of composite resins in the restoration of tooth defects has a long history and is still expanding. However, the mechanical properties of cured composite resins are still insufficient. In particular, the poor strength obstructs the application of the resins to sites subjected to a high stress, for example, the use as molar tooth crowning materials.

In recent years, clinical experts strongly demand the expansion of the use of composite resins to such high-stress sites. Therefore, the development of composite resins having higher mechanical properties is an urgent necessity. As mentioned above, the properties of cured products of polymerizable monomer compositions used for composite resins significantly affect the properties of cured products of the composite resins containing the compositions.

Techniques have been reported in which Bis-GMA and UDMA that are widely used as main components of polymerizable monomer compositions are replaced by other monomers so as to enhance the mechanical strength of cured products of composite resins (Patent Literature 1 and Patent Literature 2).

Further, techniques aiming to improve main component monomers have been reported. For example, main component monomers are improved so as to enhance the refractive index of cured products of polymerizable monomer compositions (Patent Literature 3), and main component monomers are improved so as to enhance the degree of polymerization shrinkage between before and after the curing of polymerizable monomer compositions (Patent Literature 4).

CITATION LIST

Patent Literature

Patent Literature 1: JP-A-2000-204069
Patent Literature 2: JP-A-2013-544823
Patent Literature 3: JP-A-H11-315059
Patent Literature 4: WO 2012-157566

SUMMARY OF INVENTION

Technical Problem

As already described, the expansion of the applications of dental compositions such as composite resins including polymerizable monomer compositions involves a necessity of enhancements in the mechanical properties of cured products of the dental compositions.

In view of the problems discussed above, objects of the present invention are to provide dental polymerizable monomer compositions that can give cured products having high toughness and high rigidity, and to provide dental compositions containing such dental polymerizable monomer compositions and cured products thereof having high mechanical properties.

Solution to Problem

The present inventors have found that a polymerizable monomer composition which includes a urethane acrylate obtained from an appropriately rigid diisocyanate and an appropriately flexible hydroxyacrylate can give cured products having high mechanical properties. The present inventors have also found that the mechanical properties, in particular, fracture energy and flexural breaking strength, are further enhanced by controlling the ratio of acrylate groups to methacrylate groups present in the composition to fall in a specific range. After additional extensive studies, the present inventors have completed the present invention.

The present invention provides a dental polymerizable monomer composition, a dental composition including the polymerizable monomer composition, and a cured product of the dental composition described in [1] to [12] below.

[1] A dental polymerizable monomer composition including a urethane acrylate compound (A) and a polymerizable compound (B) having at least one polymerizable group selected from methacryloyl groups and acryloyl groups, the dental polymerizable monomer composition satisfying (I) and (II) below:

(I) the urethane acrylate compound (A) is obtained by reacting a hydroxyacrylate (a1) represented by the general formula (1) below with a diisocyanate (a2) having two isocyanate groups bonded to a divalent $C_{6-9}$ aromatic hydrocarbon group or a divalent $C_{6-9}$ bridged cyclic hydrocarbon group via a methylene group optionally substituted with a hydrocarbon group;

(II) the proportion of the number of acryloyl groups present in the urethane acrylate compound (A) is 10% to less than 90% relative to the total number of methacryloyl groups and acryloyl groups in the polymerizable monomer composition;

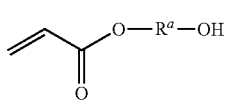
(1)

(in the general formula (1), $R^a$ represents a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom).

[2] The dental polymerizable monomer composition described in [1], wherein the proportion of the number of acryloyl groups present in the urethane acrylate compound (A) is 40% to less than 90% relative to the total number of methacryloyl groups and acryloyl groups in the polymerizable monomer composition.

[3] The dental polymerizable monomer composition described in [1], wherein the ratio of the acryloyl groups to the methacryloyl groups present in the dental polymerizable monomer composition is in the range of 10:90 to 90:10.

[4] The dental polymerizable monomer composition described in any one of [1] to [3], wherein the ratio of the acryloyl groups to the methacryloyl groups present in the dental polymerizable monomer composition is in the range of 40:60 to 90:10.

[5] The dental polymerizable monomer composition described in any one of [1] to [4], wherein the diisocyanate (a2) is at least one selected from compounds represented by the general formula (2) below:

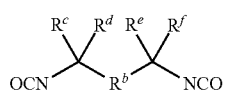
(2)

(in the general formula (2), $R^b$ represents a divalent $C_{6-9}$ aromatic hydrocarbon group or a divalent $C_{6-9}$ bridged cyclic hydrocarbon group; and $R^c$, $R^d$, $R^e$ and $R^f$ are each hydrogen or a methyl group).

[6] The dental polymerizable monomer composition described in [5], wherein the diisocyanate (a2) is at least one selected from compounds represented by the general formulas (3) to (5) below:

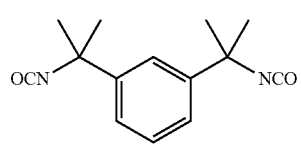
(3)

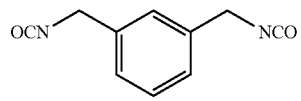
(4)

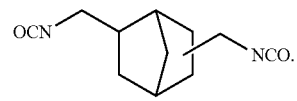
(5)

[7] The dental polymerizable monomer composition described in [6], wherein the urethane acrylate (A) is at least one compound represented by the general formula (6) below:

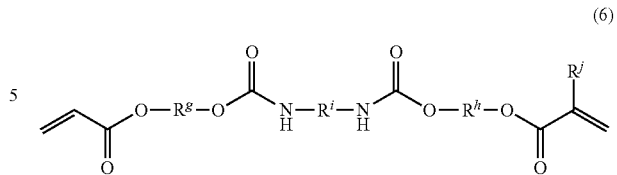
(6)

(in the general formula (6), $R^i$ is a group represented by the formula (7), (8) or (9) below; $R^g$ and $R^h$ are each independently a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom; and R represents a hydrogen atom or a methyl group);

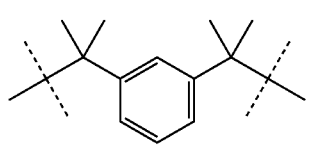
(7)

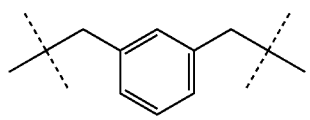
(8)

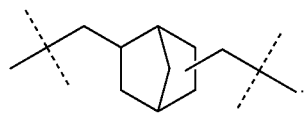
(9)

[8] The dental polymerizable monomer composition described in [1], wherein $R^a$ in the general formula (1) independently at each occurrence represents a $C_{2-6}$ linear alkylene group or a $C_{2-6}$ linear oxyalkylene group, each of which is optionally substituted with a $C_{1-3}$ alkyl group in place of a hydrogen atom.

[9] The dental polymerizable monomer composition described in [7], wherein $R^g$ and $R^h$ in the general formula (6) are each independently a $C_{2-6}$ linear alkylene group or a $C_{2-6}$ linear oxyalkylene group, each of which is optionally substituted with a $C_{1-3}$ alkyl group in place of a hydrogen atom, and R is a hydrogen atom.

[10] The dental polymerizable monomer composition described in any one of [1] to [9], wherein the viscosity at 25° C. is 1 to 100,000 mPa·s.

[11] A dental composition including the dental polymerizable monomer composition described in any one of [1] to [10], a polymerization initiator and a filler.

[12] A dental material obtained by curing the dental composition described in [11].

Advantageous Effects of Invention

The dental polymerizable monomer compositions of the invention satisfy high rigidity and high toughness when cured. Further, the dental polymerizable monomer compositions have an appropriate viscosity to exhibit excellent miscibility with fillers. Thus, the compositions are useful for dental compositions containing components such as fillers.

The dental compositions containing the inventive dental polymerizable monomer compositions can give cured products having high mechanical properties and are suited as, for example, composite resins for restoring tooth crowns and artificial tooth materials.

DESCRIPTION OF EMBODIMENTS

[Dental Polymerizable Monomer Compositions]
[Urethane Acrylates (A)]

The dental polymerizable monomer composition of the invention includes a urethane acrylate (A) that can be obtained by reacting an appropriately flexible hydroxyacrylate (a1) represented by the general formula (1) below with an appropriately rigid diisocyanate (a2). The diisocyanate (a2) has two isocyanate groups bonded to a divalent aromatic hydrocarbon group or a divalent bridged cyclic hydrocarbon group via a methylene group in which any hydrogen atom may be substituted by a hydrocarbon group.

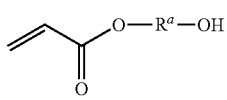
(1)

In the general formula (1), $R^a$ represents a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom.

In a preferred embodiment, $R^a$ in the general formula (1) is a $C_{2-4}$ linear alkylene group or a $C_{2-4}$ oxyalkylene group in each of which any hydrogen atom may be substituted by a $C_{1-3}$ alkyl group.

Examples of the linear alkylene groups include $-CH_2CH_2-$, $-CH_2CH_2CH_2-$, $-CH_2CH_2CH_2CH_2-$, $-CH_2CH_2CH_2CH_2CH_2-$ and $-CH_2CH_2CH_2CH_2CH_2CH_2-$. Of these, preferred linear alkylene groups are, for example, $-CH_2CH_2-$, $-CH_2CH_2CH_2-$ and $-CH_2CH_2CH_2CH_2-$.

Examples of the linear oxyalkylene groups include $-CH_2CH_2OCH_2CH_2-$ and $-CH_2CH_2OCH_2CH_2OCH_2CH_2-$. Of these, a preferred linear oxyalkylene group is, for example, $-CH_2CH_2OCH_2CH_2-$.

To ensure that the urethane acrylate (A) will exhibit appropriate flexibility, the linear alkylene group or the linear oxyalkylene group usually has 2 to 6 carbon atoms, preferably 2 to 4 carbon atoms, and more preferably 2 carbon atoms.

Examples of the alkyl groups which may substitute for hydrogen atoms in the linear alkylene group or the linear oxyalkylene group include $CH_3-$, $CH_3CH_2-$, $CH_3CH_2CH_2-$ and $(CH_3)_2CH-$. To ensure that the urethane acrylate (A) will exhibit appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms in the linear alkylene group or the linear oxyalkylene group include methacryloyloxymethylene group and acryloyloxymethylene group.

Here, the hydroxyacrylate (a1) represented by the general formula (1) has an acryloyl group. Thus, the urethane acrylate (A) always has at least one acryloyl group at a molecular terminal.

When $R^a$ is substituted with a (meth)acryloyloxymethylene group (s) and the (meth)acryloyloxymethylene group (s) is (are) the acryloyloxymethylene group(s), the polymerizable groups present in the hydroxyacrylate (a1) are all the acryloyl groups.

When, on the other hand, $R^a$ is substituted with a (meth)acryloyloxymethylene group(s) and the substituent(s) does not meet the above configuration, the polymerizable groups present in the hydroxyacrylate (a1) include both the acryloyl group(s) and the methacryloyl group(s).

In order to obtain cured products having excellent toughness, it is preferable that when the hydroxyacrylate (a1) contains a plurality of polymerizable groups, the polymerizable groups include a smaller number of methacryloyl groups and a larger number of acryloyl groups. It is more preferable that the polymerizable groups be all the acryloyl groups (the (meth)acryloyloxymethylene groups which can be present as the substituents in $R^a$ be the acryloyloxymethylene groups).

The substituent in $R^a$ preferably substitutes for a hydrogen atom on the carbon atom that is adjacent to the carbon atom in the linear alkylene group or the linear oxyalkylene group that is adjacent to the acryloyl group present in the hydroxyacrylate (a1). When, for example, the linear alkylene group is $-CH_2CH_2-$, compounds represented by the general formula (14) are preferable.

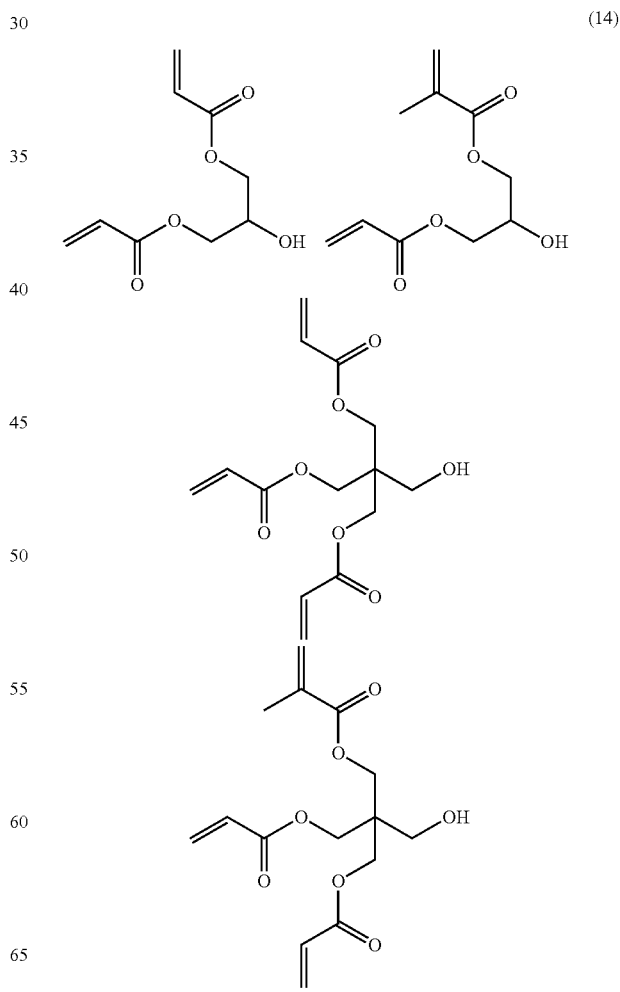
(14)

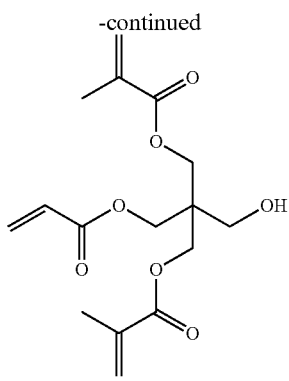

The number of the alkyl groups substituting for hydrogen atoms and the (meth)acryloyloxymethylene groups substituting for hydrogen atoms is preferably 0 to 4, although not particularly limited thereto. To ensure that the urethane acrylate (A) will exhibit appropriate flexibility, it is more preferable that the number of such substituents be 0 to 2, still more preferably 0 to 1, and particularly preferably 0, namely, no such substituents.

The hydroxyacrylates (a1) may be used singly, or two or more may be used in combination. When reacted with a diisocyanate (a2) described later, the hydroxyacrylate (a1) may be used as a mixture with a hydroxymethacrylate.

Because of the inventive dental polymerizable monomer composition containing the urethane acrylate (A), cured products of the compositions achieve both toughness and rigidity.

The detailed reasons as to why the composition can give cured products having such characteristics are not fully understood. As illustrated in, for example, the general formula (6) discussed later, the urethane acrylate (A) is composed of a moiety that is derived from the diisocyanate (a2) and includes a divalent aromatic hydrocarbon group or a divalent bridged cyclic hydrocarbon group and methylene groups in which any hydrogen atoms may be substituted by hydrocarbon groups (for example, the moiety except the NCO groups in the general formula (2), or $R^i$ in the general formula (6)) (hereinafter, this moiety is also written as the core); moieties derived from the alkylene chain in the linear portion of the hydroxyacrylate (a1) (for example, $R^a$ in the general formula (1), or $R^g$ and $R^h$ in the general formula (6)) (hereinafter, these moieties are also written as the arms); carbamoyl groups connecting the arms to the core; and at least one acryloyl group (preferably, at least two acryloyl groups at both ends).

To ensure that cured products exhibit both toughness and rigidity, it is probably necessary that the balance between a hard segment and a soft segment in (the molecule of) a polymerizable monomer be controlled appropriately.

In the case of, for example, 2,2,4-trimethylhexamethylenebis(2-carbamoyloxyethyl) dimethacrylate (UDMA) that is used frequently in the conventional techniques, the 2,2,4-trimethylhexamethylene group corresponding to the core in the invention is a $C_6$ linear alkylene group substituted with methyl groups and thus can be considered as a soft segment. The arms are ethylene groups, which can be similarly considered to be soft segments. Accordingly, UDMA has no hard segments in the molecule except the carbamoyl groups, and the molecule as a whole lacks rigidity. Consequently, cured products of dental polymerizable monomer compositions based on UDMA exhibit poor rigidity.

In contrast, the arms in the urethane acrylate (A) in the invention are alkylene chains having appropriate flexibility and can be considered as soft segments, while the core is such that a divalent aromatic hydrocarbon group (typically, an aromatic hydrocarbon group having 6 to 9 carbon atoms) or a divalent bridged cyclic hydrocarbon group (typically, a bridged cyclic hydrocarbon group having 6 to 9 carbon atoms) that can be considered to be a rigid structure is bonded to carbamoyl groups via a methylene group optionally substituted with a hydrocarbon group in place of a hydrogen atom. Thus, the core can be considered as a hard segment having appropriate rigidity. With this appropriate balance (structural characteristics) between the soft segments and the hard segment, the urethane acrylate (A) will exhibit appropriate rigidity. Thus, it is assumed that such molecules will give cured products having higher rigidity than is obtained with UDMA.

While the polymerizable groups in conventional dental polymerizable monomers are frequently methacryloyl groups, the urethane acrylate (A) in the invention contains an acryloyl group as the polymerizable group (has at least one acryloyl group, and preferably two acryloyl groups in the molecule). As mentioned hereinabove, it is probably necessary that the balance between a hard segment and a soft segment in a polymerizable monomer should be controlled appropriately in order for cured products of the polymerizable monomers to satisfy both toughness and rigidity. In general, the comparison of properties of cured products from methacrylate monomers and acrylate monomers having similar structures shows that the methacrylate monomers give rigid cured products as compared to cured products of the acrylate monomers. This fact indicates that the main chains formed by the polymerization of methacryloyl groups behave more like hard segments than soft segments, and the vice versa for the main chains resulting from the polymerization of acryloyl groups. Thus, it is assumed that the urethane acrylate (A) in the invention will give cured products having higher toughness than those from similar compounds having the methacryloyl groups alone. For the same reason, it is assumed that when the urethane acrylate (A) has more than two polymerizable groups, the obtainable cured products will exhibit higher toughness with a smaller number of methacryloyl groups and a larger number of acryloyl groups.

The diisocyanate (a2) is preferably at least one compound selected from those compounds represented by the general formula (2) below:

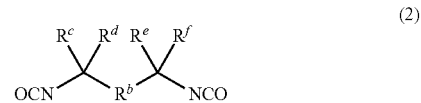

In the general formula (2), $R^b$ represents a divalent $C_{6-9}$ aromatic hydrocarbon group or a divalent $C_{6-9}$ bridged cyclic hydrocarbon group; and $R^c$, $R^d$, $R^e$ and $R^f$ are each hydrogen or a methyl group.

To ensure appropriate rigidity, the aromatic hydrocarbon group or the bridged cyclic hydrocarbon group in the diisocyanate (a2) usually has 6 to 9 carbon atoms, and preferably 6 to 7 carbon atoms. Examples of the aromatic hydrocarbon groups or the bridged cyclic hydrocarbon groups having 6 to 7 carbon atoms include phenylene group and bicyclo[2.2.1]heptylene group.

When $R^b$ is the aromatic hydrocarbon group, the two carbon atoms directly bonded to the NCO groups in the formula (2) may be present at ortho positions, meta positions or para positions with respect to each other on the benzene ring in the aromatic hydrocarbon group. To obtain the advantageous effects of the invention, it is preferable that these two carbon atoms be present at meta positions or para positions with respect to each other, and more preferably at meta positions with respect to each other.

When $R^b$ is the bridged cyclic hydrocarbon group, the two carbon atoms directly bonded to the NCO groups in the formula (2) may be present at any positions with respect to each other on the carbon ring in the bridged cyclic hydrocarbon group. To obtain the advantageous effects of the invention, it is preferable that these two carbon atoms be not bonded to the same carbon atom in the carbon ring, and it is more preferable that these carbon atoms directly bonded to the NCO groups be bonded to respective carbon atoms in the carbon ring that are separate from each other through two or more carbon atoms in the carbon ring.

The regioisomers which differ in the positions of these two carbon atoms directly bonded to the NCO groups may be used singly, or two or more kinds of such isomers may be used as a mixture.

Specifically, the diisocyanate (a2) is particularly preferably at least one compound selected from those compounds represented by the general formulas (3'), (4') and (5) below, and is most preferably at least one compound selected from those compounds represented by the general formulas (3) to (5) below.

The compound represented by the general formula (5) is called bis(isocyanatomethyl)bicyclo[2.2.1]heptane and is generally a mixture of regioisomers having the methylene groups at 2,5-positions or 2,6-positions.

The compound represented by the general formula (3') may be a mixture of regioisomers differing in the positions of the methylene groups, or may be any single type of a regioisomer isolated. In particular, the compound represented by the general formula (3) is more preferable.

The compound represented by the general formula (4') may be a mixture of regioisomers differing in the positions of the methylene groups, or may be any single type of a regioisomer isolated. In particular, the compound represented by the general formula (4) is more preferable.

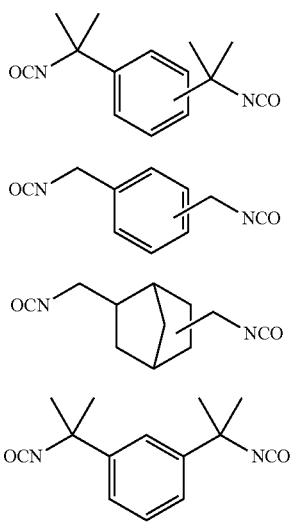

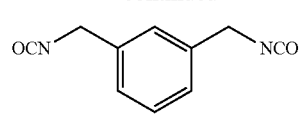

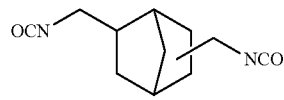

The diisocyanates (a2) may be used singly, or two or more may be used in combination.

As described hereinabove, the urethane acrylate (A) of the invention is obtained by reacting a hydroxy(meth)acrylate(s) including the hydroxyacrylate (a1) with the diisocyanate (a2). The reaction may be performed by a known method or a method in accordance with a known method.

For example, the urethane acrylate (A) of the invention may be obtained by mixing the hydroxyacrylate (a1) with the diisocyanate (a2). During this process, the hydroxyl groups in the hydroxyacrylate (a1) react with the isocyanate groups in the diisocyanate (a2) to form the carbamoyl groups. This reaction is sometimes called the urethane-forming reaction.

The reaction may be performed in the presence or absence of a catalyst. To enhance the reaction rate, a catalyst is preferably added. Known catalysts capable of accelerating the urethane-forming reaction may be used as the catalysts.

Examples of the urethane-forming catalysts include organotin compounds such as dibutyltin dilaurate, dibutyltin dioctoate and tin octanoate; organic compounds of metals other than tin such as copper naphthenate, cobalt naphthenate, zinc naphthenate, acetylacetonatozirconium, acetylacetonatoiron and acetylacetonatogermanium; amine compounds and salts thereof such as triethylamine, 1,4-diazabicyclo[2.2.2]octane, 2,6,7-trimethyl-1-diazabicyclo[2.2.2]octane, 1,8-diazabicyclo[5.4.0]undecene, N,N-dimethylcyclohexylamine, pyridine, N-methylmorpholine, N,N,N',N'-tetramethylethylenediamine, N,N,N',N'-tetramethyl-1,3-butanediamine, N,N,N',N'-pentamethyldiethylenetriamine, N,N,N',N'-tetra(3-dimethylaminopropyl)-methanediamine, N,N'-dimethylpiperazine and 1,2-dimethylimidazole; and trialkylphosphine compounds such as tri-n-butylphosphine, tri-n-hexylphosphine, tricyclohexylphosphine and tri-n-octylphosphine.

Of these, dibutyltin dilaurate and tin octanoate are advantageous in that the reaction is facilitated with a small amount of the catalyst and the catalyst has high selectivity with respect to diisocyanate compounds. When the urethane-forming catalyst is used, the amount thereof is preferably 0.001 to 0.5 wt %, more preferably 0.002 to 0.3 wt %, still more preferably 0.01 to 0.3 wt %, further preferably 0.01 to 0.2 wt %, and still further preferably 0.05 to 0.2 wt % relative to the total weight of the hydroxyacrylate (a1) and the diisocyanate (a2) taken as 100 wt %. If the amount is below the lower limit, the catalytic effect is decreased to give rise to a risk that a significantly long reaction time is incurred. If the amount is above the upper limit, the catalytic effect is so increased that the reaction generates a large amount of heat possibly to make it difficult to control the temperature. The catalyst may be added in the whole amount at the initiation of the reaction, or may be added successively or in portions to the reaction system as required. Such successive or portionwise addition of the catalyst prevents the generation of an excessively large amount of reaction heat at the initial stage of the reaction and thus facilitates the control of the reaction temperature.

The reaction temperature is not particularly limited, but is preferably 0 to 120° C., more preferably 20 to 100° C., and still more preferably 40 to 80° C. At a reaction temperature below the lower limit, the reaction rate is markedly decreased and the reaction requires a very long time to complete or does not complete at times. On the other hand, the reaction at a temperature above the upper limit may involve side reactions generating impurities. Such impurities may cause the coloration of the acrylate compound produced.

To ensure stable production at the aforementioned preferred range of temperatures, it is preferable that the reaction temperature be controlled. The urethane-forming reaction is usually exothermic. In the case where the reaction generates a large amount of heat and the temperature of the reaction product may be elevated above the preferred range of the reaction temperature, cooling is sometimes performed. When the reaction has substantially completed and the temperature of the reaction product may be decreased below the preferred range of the reaction temperature, heating is sometimes performed.

The urethane acrylate (A) has polymerization activity. Thus, undesired polymerization reaction may take place when the system is subjected to a high temperature during the production of the acrylate. To prevent such undesired polymerization reaction, a known polymerization inhibitor may be added before the initiation of the reaction or during the reaction. The polymerization inhibitor is not particularly limited as long as the inhibitor can suppress the reaction of the acrylate groups during the production of the urethane acrylate (A). Examples thereof include dibutylhydroxytoluene (BHT), hydroquinone (HQ), hydroquinone monomethyl ether (MEHQ) and phenothiazine (PTZ). Of these polymerization inhibitors, BHT is particularly preferable because the consumption of the inhibitor by the reaction with the isocyanate groups is small as compared to other phenolic polymerization inhibitors and also because the coloration encountered with amine polymerization inhibitors is small. The amount of the polymerization inhibitor added is not particularly limited, but is preferably 0.001 to 0.5 wt %, more preferably 0.002 to 0.3 wt %, still more preferably 0.005 to 0.3 wt %, further preferably 0.005 to 0.1 wt %, and still further preferably 0.01 to 0.1 wt % relative to the total weight of the hydroxyacrylate (a1) and the diisocyanate (a2) taken as 100 wt %. If the amount is below the lower limit, the polymerization inhibitor may fail to perform as expected. If the amount is above the upper limit, a dental composition containing such a urethane acrylate (A) may exhibit a markedly low curing rate and may have a limited practical applicability.

The urethane-forming reaction may involve a solvent. The solvent is not particularly limited as long as the solvent does not have practical reactivity with respect to the hydroxyacrylate (a1) and the diisocyanate (a2), does not inhibit the reaction, and can dissolve the raw materials and the product. The reaction may be performed in the absence of solvents. The hydroxyacrylate (a1) is usually a low viscous liquid and is miscible with the diisocyanate (a2) to allow the reaction to take place without solvents.

The hydroxyacrylate (a1) and the diisocyanate (a2) may be mixed with each other by any methods without limitation. For example, a controlled amount of the diisocyanate (a2) may be admixed with the hydroxyacrylate (a1) placed in a reaction vessel; a controlled amount of the hydroxyacrylate (a1) may be admixed with the diisocyanate (a2) placed in a reaction vessel; or controlled amounts of the hydroxyacrylate (a1) and the diisocyanate (a2) may be added to a reaction vessel at the same time and mixed with each other. By these mixing methods, the amount of heat generated by the urethane-forming reaction can be controlled in an appropriate range and thus the temperature control during the reaction is facilitated. Alternatively, the urethane-forming reaction may be performed in such a manner that the whole amounts of the hydroxyacrylate (a1) and the diisocyanate (a2) are added to a reaction vessel and thereafter the temperature is increased. During the reaction, the reaction temperature may be sharply increased due to the generation of reaction heat and the temperature control by cooling may be appropriately required at times.

Oxygen is effective as a polymerization inhibitor for compounds containing acryloyl groups. Thus, oxygen is sometimes introduced into the reactor to prevent undesired polymerization of acryloyl groups during the reaction. For example, oxygen may be introduced into the reactor in such a form as dried air or oxygen gas. Preferably, dried air is introduced into the reactor. For example, the dried air may be obtained by removing water using a known drying method such as the use of a condensing air dryer. In an embodiment, a mixed gas including oxygen and an inert gas such as nitrogen may be introduced into the reactor. The use of such a mixed gas including oxygen and an inert gas such as nitrogen is preferable similarly to the use of the dried air. The mixed gas including oxygen and an inert gas such as nitrogen may be obtained by mixing oxygen gas or the dried air containing oxygen with a prescribed amount of nitrogen. Here, nitrogen is preferably one that has been dehydrated by a known drying method. The method for the introduction is not particularly limited. For example, the gas may be introduced in the form of bubbles from the bottom of the reaction vessel continuously or intermittently. Alternatively, the gas may be introduced continuously or intermittently to the space at the top of the reaction vessel. The rate of the introduction of dried air may be determined appropriately in accordance with factors such as the size of the reaction vessel. When, for example, the volume of the reaction vessel is 1 L, the introduction rate is usually 1 to 500 ml/min, and preferably 1 to 300 ml/min. If the rate is below 1 ml/min, oxygen cannot be introduced in a sufficient amount and may fail to serve as the polymerization inhibitor. If the rate is above 500 ml/min, the volatilization of the diisocyanate during the reaction is increased and the properties of the urethane acrylate (A) after curing may be deteriorated.

If water is present as an impurity in the system during the urethane-forming reaction, the diisocyanate (a2) and water can react with each other to form impurities having a higher molecular weight than the target product. The increase in the amount of such impurities disadvantageously causes the increase in the viscosity of the product. Thus, it is preferable that as little water as possible be present in the reaction system during the urethane-forming reaction.

From the above aspect, the amount of water present in the hydroxyacrylate (a1) is preferably as small as possible. Specifically, the amount of water is preferably not more than 0.5 wt %, more preferably not more than 0.3 wt %, and still more preferably not more than 0.1 wt % relative to the hydroxyacrylate (a1). In the case where the hydroxyacrylate (a1) contains water in an amount exceeding the upper limit, it is preferable that the hydroxyacrylate be used as a raw material for the urethane acrylate (A) after water is removed therefrom by a known method. The reaction vessel in which the urethane-forming reaction will be performed is preferably dried by a known method to remove water therefrom.

The urethane acrylate (A) that is produced in accordance with the production method described above may be represented by the general formula (6) below.

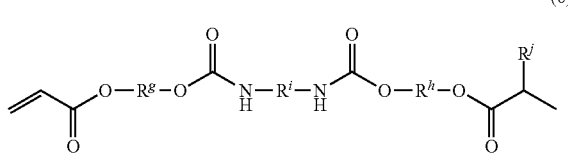

(6)

In the general formula (6), $R^g$ and $R^h$ are each a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom. In the general formula (6), $R^j$ represents a hydrogen atom or a methyl group.

In a preferred embodiment, $R^g$ and $R^h$ in the general formula (6) are each a $C_{2-4}$ linear alkylene group or a $C_{2-4}$ oxyalkylene group in each of which any hydrogen atom may be substituted by a $C_{1-3}$ alkyl group.

Examples of the linear alkylene groups include —$CH_2CH_2$—, —$CH_2CH_2CH_2$—, —$CH_2CH_2CH_2CH_2$—, —$CH_2CH_2CH_2CH_2CH_2$— and —$CH_2CH_2CH_2CH_2CH_2CH_2$—. Of these, preferred linear alkylene groups are, for example, —$CH_2CH_2$—, —$CH_2CH_2CH_2$— and —$CH_2CH_2CH_2CH_2$—. Examples of the linear oxyalkylene groups include —$CH_2CH_2OCH_2CH_2$— and —$CH_2CH_2OCH_2CH_2OCH_2CH_2$—. Of these, a preferred linear oxyalkylene group is, for example, —$CH_2CH_2OCH_2CH_2$—.

To ensure that the urethane acrylate (A) will exhibit appropriate flexibility, the linear alkylene groups or the linear oxyalkylene groups each usually have 2 to 6 carbon atoms, preferably 2 to 4 carbon atoms, and more preferably 2 carbon atoms.

Examples of the alkyl groups which may substitute for hydrogen atoms in the linear alkylene groups or the linear oxyalkylene groups include $CH_3$—, $CH_3CH_2$—, $CH_3CH_2CH_2$— and $(CH_3)_2CH$—. To ensure that the urethane acrylate (A) will exhibit appropriate flexibility, the alkyl groups preferably have 1 to 3 carbon atoms, more preferably 1 to 2 carbon atoms, and still more preferably 1 carbon atom.

Examples of the (meth)acryloyloxymethylene groups which may substitute for hydrogen atoms in the linear alkylene groups or the linear oxyalkylene groups include methacryloyloxymethylene group and acryloyloxymethylene group.

Of the urethane acrylates represented by the general formula (6), those urethane acrylates which are represented by the general formula (6') below are preferable in order to obtain the advantageous effects of the invention more effectively.

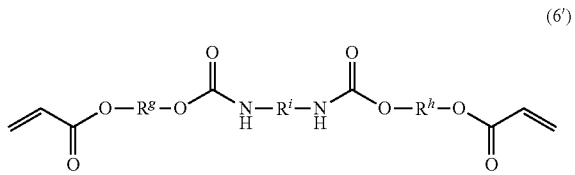

(6')

The definitions, specific examples and preferred examples of $R^i$, $R^g$ and $R^h$ in the general formula (6') are the same as those of $R^i$, $R^g$ and $R^h$ in the general formula (6).

Here, the urethane acrylate (A) represented by the general formula (6) has at least one acryloyl group at an end position. The urethane acrylate represented by the general formula (6') according to a preferred embodiment of the dental polymerizable monomer (A) has at least two acryloyl groups at both end positions.

When substituents in $R^g$ and $R^h$ are (meth)acryloyloxymethylene groups and the (meth)acryloyloxymethylene groups are the acryloyloxymethylene groups, the polymerizable groups present in the urethane acrylate (A) are all the acryloyl groups.

When, on the other hand, substituents in $R^g$ and $R^h$ are (meth)acryloyloxymethylene groups and the substituents do not meet the above configuration, the polymerizable groups present in the urethane acrylate (A) include both the acryloyl groups and the methacryloyl groups.

In order to obtain cured products having excellent toughness, it is preferable that when the urethane acrylate (A) contains three or more polymerizable groups, the polymerizable groups include a smaller number of methacryloyl groups and a larger number of acryloyl groups. It is more preferable that the polymerizable groups be all the acryloyl groups (the (meth)acryloyloxymethylene groups which can be present as the substituents in $R^g$ and $R^h$ be the acryloyloxymethylene groups).

The substituent in $R^g$ and $R^h$ each preferably substitutes for a hydrogen atom on the carbon atom that is adjacent to the carbon atom in the linear alkylene group or the linear oxyalkylene group that is adjacent to the acryloyl group at each end of the urethane acrylate (A). When, for example, the linear alkylene groups are —$CH_2CH_2$—, compounds represented by the general formula (15) are preferable.

The number of the alkyl groups substituting for hydrogen atoms and the (meth)acryloyloxymethylene groups substituting for hydrogen atoms is preferably 0 to 8, although not particularly limited thereto. To ensure that the urethane acrylate (A) will exhibit appropriate flexibility, it is more preferable that the number of such substituents be 0 to 4, still more preferably 0 to 2, and particularly preferably 0, namely, no such substituents.

In the general formula (6) or (6'), $R^i$ is a group bonded to the nitrogen atoms in the two adjacent carbamoyl groups, and has a divalent aromatic hydrocarbon group or a divalent bridged cyclic hydrocarbon group in the middle and has two methylene groups which are each bonded to the nitrogen atom in the carbamoyl group and to the divalent group and in which any hydrogen atom may be substituted by a methyl group (hereinafter, such methylene group is also written as the methylene group A).

To ensure appropriate rigidity, the aromatic hydrocarbon group or the bridged cyclic hydrocarbon group in $R^i$ usually has 6 to 9 carbon atoms, and preferably 6 to 7 carbon atoms. Examples of the aromatic hydrocarbon groups or the bridged cyclic hydrocarbon groups having 6 to 7 carbon atoms include phenylene group and bicyclo[2.2.1]heptylene group.

When the group in $R^i$ that is bonded to the two methylene groups A is the aromatic hydrocarbon group, the two methylene groups A may be present at ortho positions, meta positions or para positions with respect to each other on the benzene ring in the aromatic hydrocarbon group. To obtain the advantageous effects of the invention, it is preferable that these two methylene groups A be present at meta positions or para positions with respect to each other, and more preferably at meta positions with respect to each other.

When the group in $R^i$ that is bonded to the two methylene groups A is the bridged cyclic hydrocarbon group, the two methylene groups A may be present at any positions with respect to each other on the carbon ring in the bridged cyclic hydrocarbon group. To obtain the advantageous effects of the invention, it is preferable that these two methylene groups A be not bonded to the same carbon atom in the carbon ring, and it is more preferable that these methylene groups A be bonded to respective carbon atoms in the carbon ring that are separate from each other through two or more carbon atoms in the carbon ring.

The regioisomers differing in the positions of these two methylene groups A may be used singly, or two or more kinds of such isomers may be used as a mixture.

Specifically, $R^i$ is particularly preferably a group selected from those groups represented by the general formulas (7'), (8') and (9) below, and is most preferably a group selected from those groups represented by the general formulas (7) to (9) below.

In the case of the group represented by the general formula (9), the group is generally derived from a mixture of regioisomers having the methylene groups at 2,5-positions or 2,6-positions.

In the case of the group represented by the general formula (7'), the group may be derived from a mixture of regioisomers differing in the positions of the methylene groups, or may be derived from any single type of a regioisomer isolated. In particular, the group represented by the general formula (7) is more preferable.

In the case of the group represented by the general formula (8'), the group may be derived from a mixture of regioisomers differing in the positions of the methylene groups, or may be derived from any single type of a regioisomer isolated. In particular, the group represented by the general formula (8) is more preferable.

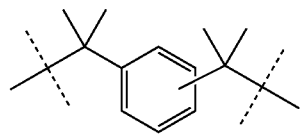

(7')

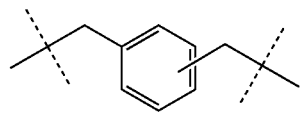

(8')

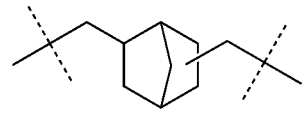

(9)

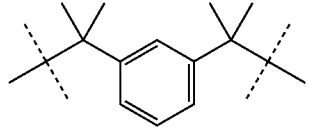

(7)

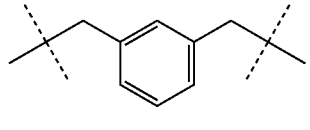

(8)

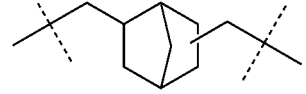

(9)

Of the urethane acrylates (A), those urethane acrylates represented by the following chemical formulas are preferable.

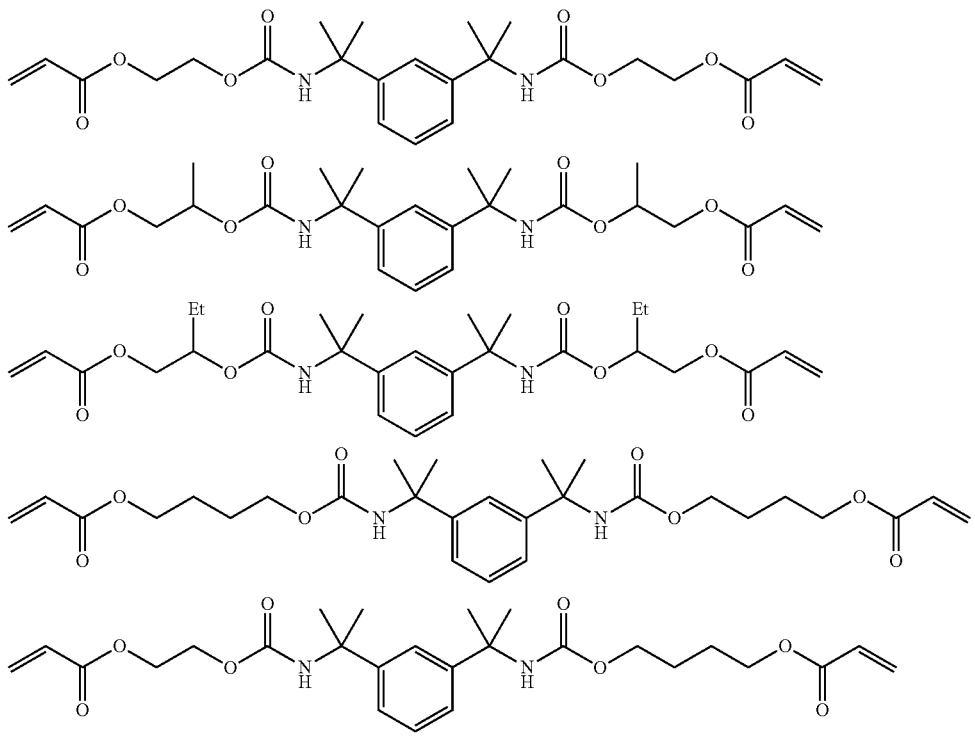

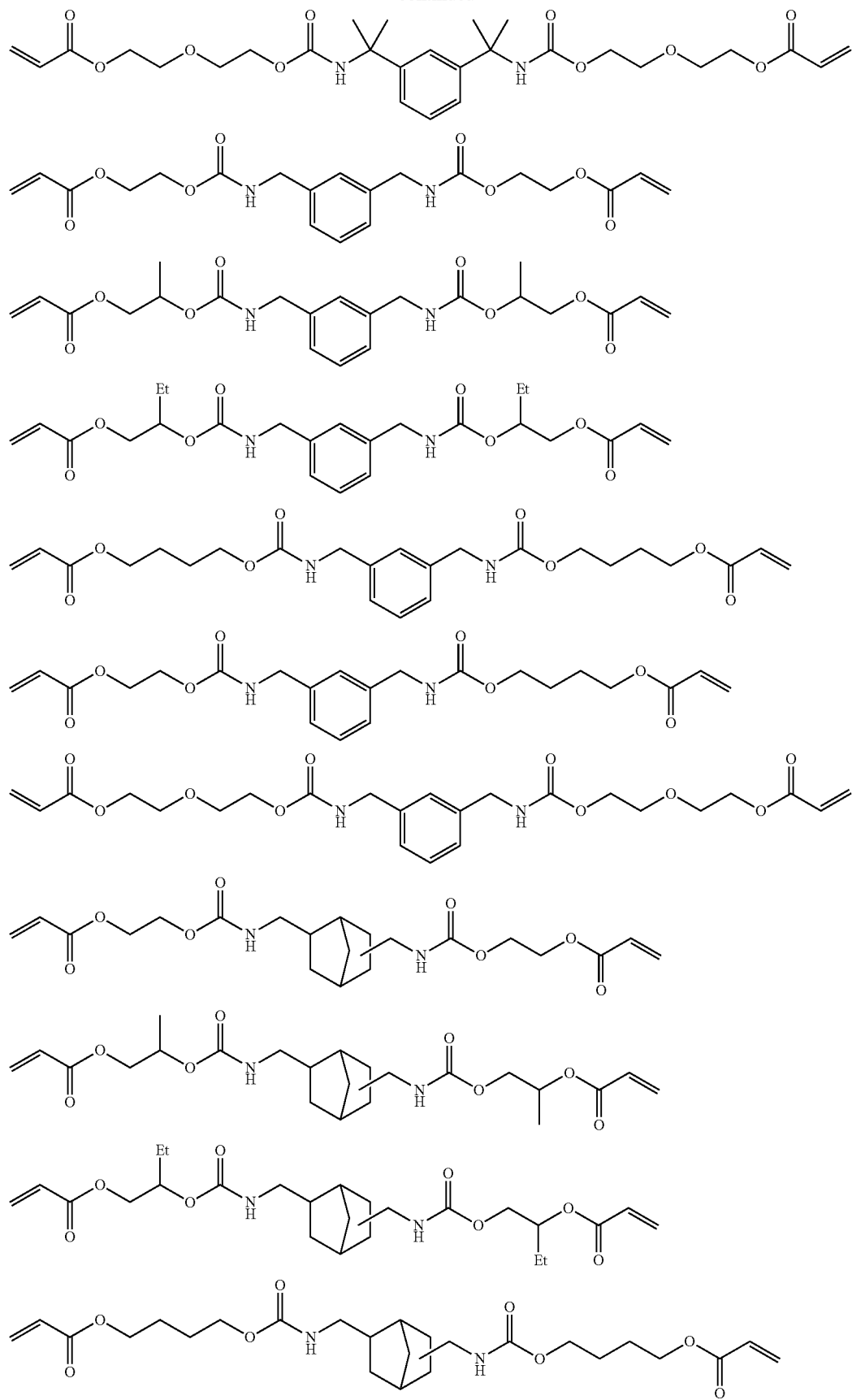

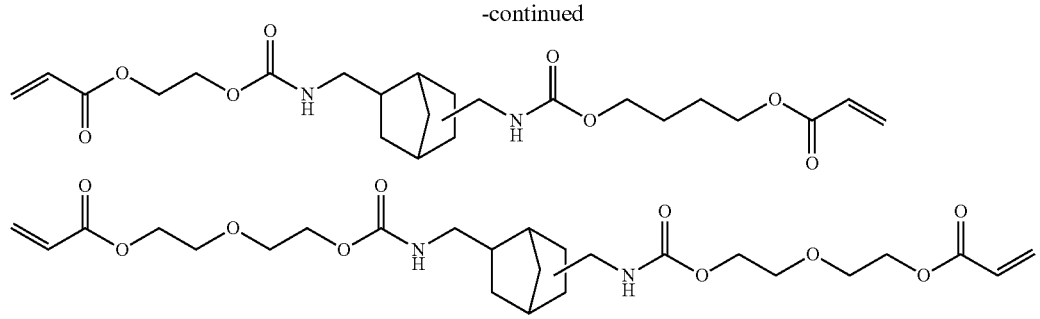

In the above formulas, Et indicates an ethyl group.

The molecular weight of the urethane acrylate (A) depends on the structure, but is generally about 400 to 1000, and preferably 400 to 700. When the molecular weight is in this range, the monomer exhibits a low viscosity to provide an advantage in the preparation of a dental composition.

Further, the urethane acrylate (A) is preferably liquid at room temperature. The viscosity of the urethane acrylate (A) at 65° C. is preferably 1 to 50000 mPa·s, more preferably 1 to 20000 mPa·s, and still more preferably 1 to 5000 mPa·s. When the viscosity is in this range, the dental polymerizable monomer composition exhibits a low viscosity to provide an advantage in the preparation of a dental composition. The urethane acrylate (A) sometimes contains minor components other than the desired urethane acrylate (A), such as oligomers formed during storage at high temperatures and highly viscous byproduct compounds. However, the presence of such minor components tends to be an insignificant problem in the use of a dental composition as long as the viscosity is in the aforementioned range. The viscosity is a value measured at 65° C. with a cone-plate viscometer (for example, TVE-22H manufactured by TOKI SANGYO CO., LTD.).

The urethane acrylates (A) may be used singly, or two or more may be used in combination. For example, the dental polymerizable monomer composition will contain two or more kinds of the dental polymerizable monomers (A) when the dental polymerizable monomers (A) are prepared using two or more kinds of hydroxyacrylates (a1), and a diisocyanate(s) (a2) as the raw materials, or when the dental polymerizable monomers (A) are prepared using a mixture of a hydroxyacrylate (a1) and a hydroxymethacrylate, and a diisocyanate(s) (a2) as the raw materials.

[Polymerizable Compounds (B)]

In addition to the urethane acrylate (A) described above, the dental polymerizable monomer composition of the invention contains a polymerizable compound (B) (except the urethane acrylates (A)) having at least one polymerizable group selected from methacryloyl groups and acryloyl groups.

The number of the polymerizable groups present in the polymerizable compound (B) may be 1, or may be 2 or greater. The number of the polymerizable groups is preferably 2 to 10. The number of the polymerizable groups is more preferably 2 to 6. The number of the polymerizable groups is still more preferably 2 to 4.

The molecular weight of the polymerizable compound (B) is preferably 80 to 1000, and more preferably 150 to 700. If the molecular weight is below this range, the compound has a low boiling point. Thus, the above lower limit is advantageous from the point of view of handling properties in the preparation of a dental composition. If the molecular weight is higher than the above range, the compound tends to exhibit a high viscosity. Thus, the above upper limit is advantageous from the point of view of handling properties in the preparation of a dental composition.

The polymerizable compound (B) is preferably liquid at room temperature. The viscosity of the polymerizable compound (B) at 65° C. is preferably 1 to 50000 mPa·s, more preferably 1 to 20000 mPa·s, still more preferably 1 to 5000 mPa·s, and particularly preferably 1 to 3000 mPa·s. When the viscosity is in this range, the dental polymerizable monomer composition exhibits a low viscosity to provide an advantage in the preparation of a dental composition. Further, the viscosity of the polymerizable compound (B) at 65° C. is preferably lower than the viscosity of the urethane acrylate (A) at 65° C. The polymerizable compound (B) sometimes contains minor components other than the desired polymerizable compound (B), such as oligomers formed during storage at high temperatures. However, the presence of such minor components tends to be an insignificant problem in the use of a dental composition as long as the viscosity is in the aforementioned range. The viscosity is a value measured at 65° C. with a cone-plate viscometer.

A single polymerizable compound (B) may be used, or two or more kinds of such compounds may be used in combination.

Examples of the polymerizable compounds (B) having one polymerizable group include those polymerizable compounds represented by the general formula (10) below.

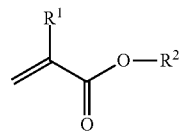

(10)

In the general formula (10), $R^1$ is hydrogen or a methyl group, and $R^2$ is a $C_{1-20}$ monovalent organic group which may contain oxygen or nitrogen.

Examples of the monovalent organic groups include hydrocarbon groups such as $C_{1-20}$ acyclic hydrocarbon groups, for example, alkyl groups, alkenyl groups and alkynyl groups, and $C_{1-20}$ cyclic hydrocarbon groups, for example, cycloalkyl groups, cycloalkenyl groups, cycloalkynyl groups and aryl groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, alkoxyalkyl groups, alkoxyalkylene glycol groups and tetrahydrofurfuryl groups.

The C$_{1-20}$ cyclic hydrocarbon groups may have acyclic hydrocarbon moieties. Further, the acyclic hydrocarbon moieties present in these groups may be linear or branched.

In the case where the C$_{1-20}$ hydrocarbon groups or the C$_{1-20}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the C$_{1-20}$ hydrocarbon groups and the C$_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl-containing compounds represented by the general formula (10) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate and 1,4-cyclohexanedimethanol monomethacrylate.

Examples of the acryloyl-containing compounds represented by the general formula (10) include methyl acrylate, ethyl acrylate, propyl acrylate, butyl acrylate, hexyl acrylate, cyclohexyl acrylate, ethoxydiethylene glycol acrylate, methoxytriethylene glycol acrylate, phenoxyethyl acrylate, 2-hydroxyethyl acrylate, 2-hydroxypropyl acrylate, 2-hydroxybutyl acrylate, 2-hydroxy-3-phenoxypropylacrylate, 4-hydroxybutyl acrylate and 1,4-cyclohexanedimethanol monoacrylate.

Examples of the polymerizable compounds (B) having two or more polymerizable groups include those polymerizable compounds represented by the general formula (11) below.

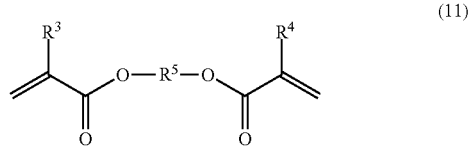

(11)

In the general formula (11), R$^3$ and R$^4$ each represent hydrogen or a methyl group and may be the same as or different from each other; and R$^5$ represents a C$_{1-40}$ divalent organic group which may contain oxygen or nitrogen. The urethane acrylate compounds (A) are not categorized as the compounds represented by the general formula (11).

Examples of the divalent organic groups include hydrocarbon groups, for example, C$_{1-40}$ acyclic hydrocarbon groups such as alkylene groups, alkenylene groups and alkynylene groups, and C$_{1-40}$ cyclic hydrocarbon groups such as cycloalkylene groups, cycloalkenylene groups, cycloalkynylene groups and arylene groups; and C$_{1-40}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The C$_{1-40}$ cyclic hydrocarbon groups may have acyclic hydrocarbon moieties. Further, the acyclic hydrocarbon moieties present in these groups may be linear or branched.

In the case where the C$_{1-40}$ hydrocarbon groups or the C$_{1-40}$ oxygen-containing hydrocarbon groups contain linear alkylene moieties, at least one of the methylene groups in such moieties may be substituted by an ester bond, an amide bond, a carbonate bond, a urethane bond (a carbamoyl group) or a urea bond (but the methylene groups are not substituted contiguously).

Further, hydrogen atoms present in the organic groups such as the C$_{1-40}$ hydrocarbon groups and the C$_{1-40}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

Among the polymerizable compounds represented by the general formula (11), some preferred polymerizable compounds are those polymerizable compounds in which R$^5$ is a linear alkylene group having 2 to 20 carbon atoms, desirably 4 to 12 carbon atoms.

Examples of the compounds which correspond to the above preferred polymerizable compounds and have methacryloyl groups include 1,4-butanediol dimethacrylate, 1,6-hexanediol dimethacrylate, 1,8-octanediol dimethacrylate, 1,9-nonanediol dimethacrylate and 1,10-decanediol dimethacrylate.

Examples of the compounds which correspond to the above preferred polymerizable compounds and have acryloyl groups include 1,4-butanediol diacrylate, 1,6-hexanediol diacrylate, 1,8-octanediol diacrylate, 1,9-nonanediol diacrylate and 1,10-decanediol diacrylate.

Among the polymerizable compounds represented by the general formula (11), other preferred polymerizable compounds are those polymerizable compounds in which R$^5$ is a linear oxyalkylene group having 2 to 20 carbon atoms, desirably 4 to 12 carbon atoms.

Examples of the compounds which correspond to the above preferred polymerizable compounds and have methacryloyl groups include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate and polypropylene glycol dimethacrylate.

Examples of the compounds which correspond to the above preferred polymerizable compounds and have acryloyl groups include ethylene glycol diacrylate, diethylene glycol diacrylate, triethylene glycol diacrylate, tetraethylene glycol diacrylate, polyethylene glycol diacrylate, tripropylene glycol diacrylate, tetrapropylene glycol diacrylate and polypropylene glycol diacrylate.

Among the polymerizable compounds represented by the general formula (11), other preferred polymerizable compounds are carbamoyl group-containing polymerizable compounds represented by the general formula (12) below. The urethane acrylate compounds (A) are not categorized as the compounds represented by the general formula (12).

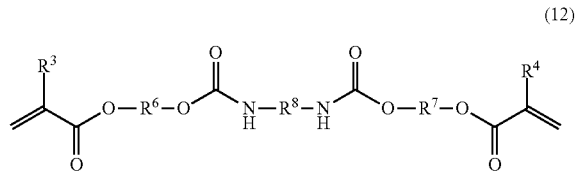

(12)

In the general formula (12), $R^3$ and $R^4$ each represent hydrogen or a methyl group and may be the same as or different from each other; and $R^6$ and $R^7$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (12), $R^8$ represents a $C_{1-20}$ divalent organic group which may contain oxygen. Examples of the divalent organic groups include $C_{1-20}$ acyclic hydrocarbon groups such as alkylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ acyclic hydrocarbon groups may have acyclic hydrocarbon moieties. Further, the acyclic hydrocarbon moieties present in these groups may be linear or branched.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (12) include urethane methacrylates formed by the reaction between a hydroxymethacrylate such as 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate or 1,4-cyclohexanedimethanol monomethacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane methacrylates include 2,2,4-trimethylhexamethylene bis(2-carbamoyloxyethyl) dimethacrylate (UDMA).

Examples of the acryloyl group-containing compounds represented by the general formula (12) include urethane acrylates formed by the reaction between a hydroxyacrylate such as 2-hydroxyethyl acrylate, 2-hydroxypropyl acrylate, 2-hydroxybutyl acrylate, 2-hydroxy-3-phenoxypropylacrylate, 4-hydroxybutyl acrylate or 1,4-cyclohexanedimethanol monoacrylate, and a diisocyanate such as 2,4- or 2,6-toluene diisocyanate, 4,4'-, 2,4'- or 2,2'-diphenylmethane-diisocyanate, 1,6-hexamethylene diisocyanate, or 2,2,4- or 2,4,4-trimethyl-1,6-hexamethylene-diisocyanate. Examples of such urethane acrylates include 2,2,4-trimethylhexamethylene bis(2-carbamoyloxyethyl) diacrylate).

Among the polymerizable compounds represented by the general formula (11), other preferred compounds are those polymerizable compounds represented by the general formula (13) below.

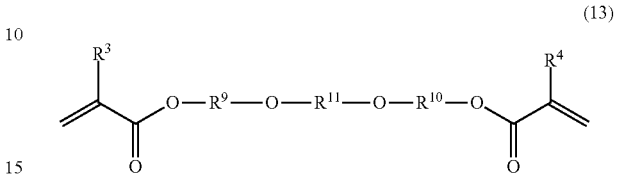

(13)

In the general formula (13), $R^3$ and $R^4$ each represent hydrogen or a methyl group and may be the same as or different from each other; and $R^9$ and $R^{10}$ each represent a $C_{1-12}$ divalent organic group which may contain oxygen, and may be the same as or different from each other.

Examples of the divalent organic groups include hydrocarbon groups, for example, $C_{1-12}$ acyclic hydrocarbon groups such as alkylene groups, and $C_{1-12}$ cyclic hydrocarbon groups such as cycloalkylene groups and arylene groups; and $C_{1-12}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-12}$ cyclic hydrocarbon groups may have acyclic hydrocarbon moieties. Further, the acyclic hydrocarbon moieties present in these groups may be linear or branched.

Further, hydrogen atoms present in the organic groups such as the $C_{1-12}$ hydrocarbon groups and the $C_{1-12}$ oxygen-containing hydrocarbon groups may be substituted by acid groups such as carboxyl groups and phosphate groups, functional groups such as hydroxyl groups, amino groups and epoxy groups, and polymerizable groups such as acryloyl groups and methacryloyl groups.

In the general formula (13), $R^{11}$ represents a $C_{1-20}$ divalent organic group which may contain oxygen.

Examples of the divalent organic groups include $C_{1-20}$ hydrocarbon groups such as alkylene groups, cycloalkylene groups and arylene groups; and $C_{1-20}$ oxygen-containing hydrocarbon groups such as those groups corresponding to the above hydrocarbon groups except that oxygen is introduced between at least part of the carbon atoms forming carbon-carbon bonds (but oxygen atoms are not inserted contiguously), for example, oxyalkylene groups. The $C_{1-20}$ cyclic hydrocarbon groups may have acyclic hydrocarbon moieties.

Further, hydrogen atoms present in the organic groups such as the $C_{1-20}$ hydrocarbon groups and the $C_{1-20}$ oxygen-containing hydrocarbon groups may be substituted by acid groups such as carboxyl groups and phosphate groups, and functional groups such as hydroxyl groups, amino groups and epoxy groups.

Examples of the methacryloyl group-containing compounds represented by the general formula (13) include 2,2-bis[4-(3-methacryloyloxy-2-hydroxypropoxy)phenyl] propane (Bis-GMA), ethylene oxide-modified bisphenol A dimethacrylate and propylene oxide-modified bisphenol A dimethacrylate.

Examples of the acryloyl group-containing compounds represented by the general formula (13) include 2,2-bis[4-(3-acryloyloxy-2-hydroxypropoxy)phenyl]propane, ethylene oxide-modified bisphenol A diacrylate and propylene oxide-modified bisphenol A diacrylate.

When the dental polymerizable monomer composition of the invention is used in such an application as dental adhesives, it is preferable that the composition contain a polymerizable compound (B) exhibiting a bonding function. Examples of such adhesive polymerizable compounds (B) include those polymerizable compounds having at least one polymerizable group selected from methacryloyl groups and acryloyl groups, and an acidic group. Examples of the acidic groups include phosphate residues, pyrophosphate residues, thiophosphate residues, carboxylate residues and sulfonate residues.

Examples of the polymerizable compounds having a methacryloyl group and a phosphate residue include 2-methacryloyloxyethyl dihydrogen phosphate, 9-methacryloyloxynonyl dihydrogen phosphate, 10-methacryloyloxydecyl dihydrogen phosphate, 11-methacryloyloxyundecyl dihydrogen phosphate, 20-methacryloyloxyeicosyl dihydrogen phosphate, 1,3-dimethacryloyloxypropyl-2-dihydrogen phosphate, 2-methacryloyloxyethyl phenyl phosphoric acid, 2-methacryloyloxyethyl 2'-bromoethyl phosphoric acid, methacryloyloxyethyl phenyl phosphonate, and acid chlorides of these compounds.

Examples of the polymerizable compounds having an acryloyl group and a phosphate residue include 2-acryloyloxyethyl dihydrogen phosphate, 9-acryloyloxynonyl dihydrogen phosphate, 10-acryloyloxydecyl dihydrogen phosphate, 11-acryloyloxyundecyl dihydrogen phosphate, 20-acryloyloxyeicosyl dihydrogen phosphate, 1,3-diacryloyloxypropyl-2-dihydrogen phosphate, 2-acryloyloxyethyl phenyl phosphoric acid, 2-acryloyloxyethyl 2'-bromoethyl phosphoric acid, acryloyloxyethyl phenyl phosphonate, and acid chlorides of these compounds.

Examples of the polymerizable compounds having a methacryloyl group and a pyrophosphate residue include di(2-methacryloyloxyethyl) pyrophosphate, and acid chlorides thereof.

Examples of the polymerizable compounds having an acryloyl group and a pyrophosphate residue include di(2-acryloyloxyethyl) pyrophosphate, and acid chlorides thereof.

Examples of the polymerizable compounds having a methacryloyl group and a thiophosphate residue include 2-methacryloyloxyethyl dihydrogen dithiophosphate, 10-methacryloyloxydecyl dihydrogen thiophosphate, and acid chlorides of these compounds.

Examples of the polymerizable compounds having an acryloyl group and a thiophosphate residue include 2-acryloyloxyethyl dihydrogen dithiophosphate, 10-acryloyloxydecyl dihydrogen thiophosphate, and acid chlorides of these compounds.

Examples of the polymerizable compounds having a methacryloyl group and a carboxylate residue include 4-methacryloyloxyethoxycarbonylphthalic acid, 5-methacryloylaminopentylcarboxylic acid, 11-methacryloyloxy-1,1-undecanedicarboxylic acid, and acid chlorides and acid anhydrides of these compounds.

Examples of the polymerizable compounds having an acryloyl group and a carboxylate residue include 4-acryloyloxyethoxycarbonylphthalic acid, 5-acryloylaminopentylcarboxylic acid, 11-acryloyloxy-1,1-undecanedicarboxylic acid, and acid chlorides and acid anhydrides of these compounds.

Examples of the polymerizable compounds having a methacryloyl group and a sulfonate residue include 2-sulfoethyl methacrylate and 2-methacrylamido-2-methylpropanesulfonic acid.

Examples of the polymerizable compounds having an acryloyl group and a sulfonate residue include 2-sulfoethyl acrylate and 2-acrylamido-2-methylpropanesulfonic acid.

The dental polymerizable monomer composition of the invention may include an acidic group-containing polymerizable compound which is not categorized into the polymerizable compounds (B). Examples of such acidic group-containing polymerizable compounds include sulfonate residue-containing polymerizable compounds such as styrenesulfonic acid. The acidic group-containing polymerizable monomers may be used singly, or two or more may be used in combination.

When the dental polymerizable monomer composition of the invention contains such an acidic group-containing polymerizable compound, the acidic group-containing polymerizable compound may be added in any amount without limitation. Usually, the dental polymerizable monomer composition contains the acidic group-containing polymerizable compound in such an amount that the number of the polymerizable groups present in the acidic group-containing polymerizable compound is not more than 50% relative to the total number of the polymerizable groups in the dental polymerizable monomer composition.

The number of the acryloyl groups present in the urethane acrylate (A) constituting the inventive dental polymerizable monomer composition is not less than 10%, preferably not less than 20%, and more preferably not less than 40% relative to the total number of the methacryloyl groups and the acryloyl groups present in the dental polymerizable monomer composition. The number of the acryloyl groups present in the urethane acrylate (A) is 10% to less than 90%, preferably 20% to less than 90%, and more preferably 40% to less than 90% relative to the total number of the methacryloyl groups and the acryloyl groups present in the dental polymerizable monomer composition. In another preferred embodiment, the number of the acryloyl groups present in the urethane acrylate (A) is preferably 20% to less than 80%, and more preferably 40% to less than 80% relative to the total number of the methacryloyl groups and the acryloyl groups present in the dental polymerizable monomer composition. Here, the number of the acryloyl groups in the dental polymerizable monomer composition refers to the total number of the acryloyl groups present in the urethane acrylate (A) and the polymerizable compound (B). The incorporation of the urethane acrylate (A) in the above amount ensures that the inventive dental polymerizable monomer composition will give cured products which exhibit excellent mechanical characteristics with toughness ascribed to the acrylate and rigidity provided by the methacrylate.

In the dental polymerizable monomer composition of the invention, it is preferable that both an acryloyl group-containing compound and a methacryloyl group-containing compound be present in the composition. Thus, it is preferable that the polymerizable compound(s) (B) includes at least a methacryloyl group-containing polymerizable compound. The ratio of the number of the acryloyl groups to the number of the methacryloyl groups in the dental polymerizable monomer composition is preferably in the range of 10:90 to 90:10, more preferably in the range of 20:80 to 90:10, and still more preferably in the range of 40:60 to 90:10. In another preferred embodiment, the ratio of the number of the acryloyl groups to the number of the methacryloyl groups in the dental polymerizable monomer composition is preferably in the range of 20:80 to 80:20, and more preferably in the range of 40:60 to 80:20. Here, the number of the acryloyl groups in the dental polymerizable monomer composition refers to the total number of the acryloyl groups present in the urethane acrylate (A) and any polymerizable compound (B), and the number of the methacryloyl groups indicates the total number of the methacryloyl groups present in the polymerizable compound (B).

The acryloyl to methacryloyl numerical ratio may be appropriately controlled to fall in the specific range by mixing the methacryloyl group-containing polymerizable compound and the acryloyl group-containing polymerizable compound with each other in a desired ratio.

As described hereinabove, main chains formed by the polymerization of methacryloyl groups behave more like hard segments than soft segments, and the vice versa for main chains resulting from the polymerization of acryloyl groups. Thus, it is assumed that the balance of soft segment properties and hard segment properties ascribed to the natures of these two types of polymerizable groups can be controlled appropriately by appropriately manipulating the ratio of the number of the acryloyl groups to the number of the methacryloyl groups present in the dental polymerizable monomer composition in the manner described above. Further, it is known that acryloyl groups and methacryloyl groups have significantly different polymerization rates. Thus, acryloyl groups and methacryloyl groups present in a polymerizable monomer composition will form a copolymer including the respective blocks. Such block copolymerization probably occurs also during the curing of the inventive dental polymerizable monomer composition. It is probable that the block copolymerization results in a cured product in which soft domains and hard domains are separate from each other to a degree, and the toughness and rigidity of the cured product are satisfied by virtue of the balanced presence of these domains.

The viscosity of the inventive dental polymerizable monomer composition is not particularly limited, but is preferably in the range of 1 to 100,000 mPa·s at 25° C., more preferably in the range of 5 to 60,000 mPa·s, still more preferably in the range of 10 to 30,000 mPa·s, and further preferably in the range of 100 to 10,000 mPa·s. If the viscosity is above the upper limit, the dental polymerizable monomer composition does not allow components such as fillers to be dispersed therein efficiently during the production of the inventive dental composition, possibly resulting in a failure to obtain a uniform mixture. If, on the other hand, the viscosity is less than the lower limit, the dental polymerizable monomer composition will contain an increased amount of air bubbles when components such as fillers are admixed therewith during the production of the inventive dental composition, possibly resulting in a failure to obtain a uniform mixture. The polymerizable monomer composition is sometimes partially oligomerized during storage at high temperatures. The viscosity discussed here is a value immediately after the production of the polymerizable monomer composition before the occurrence of any oligomerization.

In the invention, the hue of the dental polymerizable monomer composition is not particularly limited, but is preferably one suited for use as a raw ingredient for dental materials. Specifically, the APHA scale is preferably not more than 500, more preferably not more than 200, and still more preferably not more than 100.

In the production of the inventive dental polymerizable monomer composition, the urethane acrylate (A) and the polymerizable compound (B) may be mixed together by any method without limitation. For example, the inventive dental polymerizable monomer composition may be obtained by adding the urethane acrylate (A) and the polymerizable compound (B) into a container and stirring the mixture to uniformity while performing heating appropriately.

To obtain an enhancement in storage stability, the dental polymerizable monomer composition of the invention may contain the polymerization inhibitor described hereinabove. The inhibitor may be added during the synthesis of the urethane acrylate (A) as mentioned hereinabove, or may be added during a downstream step as required.

By the addition of a polymerization initiator described later, the dental polymerizable monomer composition of the invention comes to exhibit polymerizability at normal or elevated temperatures or upon illumination. Cured products of the inventive dental polymerizable monomer compositions have high mechanical properties as compared to cured products of conventional dental polymerizable monomer compositions, and in particular have high and well-balanced flexural breaking strength and fracture energy. In other words, the cured products are materials that exhibit both toughness and rigidity.

The dental polymerizable monomer composition of the invention may further contain additives such as fungicides, disinfectants, stabilizers and preservatives as required while still ensuring that the advantageous effects of the invention are not impaired.

[Dental Compositions]

The dental polymerizable monomer composition of the invention may be suitably used as a component for the inventive dental composition. The dental composition includes the dental monomer composition described hereinabove, a polymerization initiator and a filler. The dental composition has cold- or room temperature-polymerizability, thermal polymerizability, or photopolymerizability, and may be suitably used as, for example, a dental restorative material.

The polymerization initiator may be any of general polymerization initiators used in the dental field, and is usually selected in consideration of the polymerizability of the polymerizable monomers, and the polymerization conditions.

In the case of self curing, for example, a redox polymerization initiator that is a combination of an oxidant and a reductant is preferable. When using a redox polymerization initiator, an oxidant and a reductant which are separately packaged need to be mixed with each other immediately before use.

The oxidants are not particularly limited. Examples include organic peroxides such as diacyl peroxides, peroxy esters, dialkyl peroxides, peroxyketals, ketone peroxides and hydroperoxides. Examples of the organic peroxides include such diacyl peroxides as benzoyl peroxide, 2,4-dichlorobenzoyl peroxide and m-toluoyl peroxide; such peroxy esters as t-butyl peroxybenzoate, bis-t-butyl peroxyisophthalate, 2,5-dimethyl-2,5-bis(benzoylperoxy)hexane, t-butyl peroxy-2-ethylhexanoate and t-butyl peroxyisopropyl carbonate; such dialkyl peroxides as dicumyl peroxide, di-t-butyl peroxide and lauroyl peroxide; such peroxyketals as 1,1-bis(t-butylperoxy)-3,3,5-trimethylcyclohexane; such ketone peroxides as methyl ethyl ketone peroxide; and such hydroperoxides as t-butyl hydroperoxide.

The reductants are not particularly limited, but tertiary amines are usually used. Examples of the tertiary amines include N,N-dimethylaniline, N,N-dimethyl-p-toluidine, N,N-dimethyl-m-toluidine, N,N-diethyl-p-toluidine, N,N- dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-p-toluidine, N,N-bis(2-hydroxyethyl)-3,5-dimethylaniline, N,N-bis(2-hydroxyethyl)-3,4-dimethylaniline, N,N-bis(2-hydroxyethyl)-4-ethylaniline, N,N-bis(2-hydroxyethyl)-4-i-propylaniline, N,N-bis(2-hydroxyethyl)-4-t-butylaniline, N,N-di(2-hydroxyethyl)-3,5-di-i-propylaniline, N,N-bis(2-hydroxyethyl)-3,5-di-t-butylaniline, ethyl 4-dimethylaminobenzoate, n-butoxyethyl 4-dimethylaminobenzoate, (2-methacryloyloxy)ethyl 4-dimethylaminobenzoate, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N,N-bis(methacryloyloxyethyl)-N-methylamine, N,N-bis(methacryloyloxyethyl)-N-ethylamine, N,N-bis(2-hydroxyethyl)-N-methacryloyloxyethylamine, N,N-bis(methacryloyloxyethyl)-N-(2-hydroxyethyl)amine and tris(methacryloyloxyethyl)amine.

Besides these organic peroxide/amine systems, other redox polymerization initiators such as cumene hydroperoxide/thiourea systems, ascorbic acid/$Cu^{2+}$ salt systems and organic peroxide/amine/sulfinic acid (or sulfinate salt) systems may be used. Further, other polymerization initiators such as tributyl borane and organic sulfinic acids are also suitably used.

In the case of thermal polymerization with heating, it is preferable to use peroxides or azo compounds.

The peroxides are not particularly limited, and examples include benzoyl peroxide, t-butyl hydroperoxide and cumene hydroperoxide. The azo compounds are not particularly limited, and examples include azobisisobutyronitrile.

In the case of photopolymerization with the application of visible lights, suitable initiators are redox initiators such as α-diketones/tertiary amines, α-diketones/aldehydes and α-diketones/mercaptans.

Examples of the photopolymerization initiators, although not particularly limited to, include α-diketones/reductants, ketals/reductants and thioxanthones/reductants. Examples of the α-diketones include camphorquinone, benzil and 2,3-pentanedione. Examples of the ketals include benzyl dimethyl ketal and benzyl diethyl ketal. Examples of the thioxanthones include 2-chlorothioxanthone and 2,4-diethylthioxanthone. Examples of the reductants include tertiary amines such as Michler's ketone, 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine and dimethylaminophenanthrol; aldehydes such as citronellal, lauryl aldehyde, phthalic dialdehyde, dimethylaminobenzaldehyde and terephthalaldehyde; and thiol group-containing compounds such as 2-mercaptobenzoxazole, decanethiol, 3-mercaptopropyltrimethoxysilane, 4-mercaptoacetophenone, thiosalicylic acid and thiobenzoic acid. Organic peroxides may be added to these redox systems. That is, α-diketone/organic peroxide/reductant systems may be suitably used.

In the case of photopolymerization with the application of UV lights, some suitable initiators are benzoin alkyl ethers and benzyl dimethyl ketal. Further, such photopolymerization initiators as (bis)acylphosphine oxides are also suitably used.

Of the (bis)acylphosphine oxides, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide and benzoyldi-(2,6-dimethylphenyl) phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide and (2,5,6-trimethylbenzoyl)-2,4,4-trimethylpentylphosphine oxide. These (bis)acylphosphine oxide photopolymerization initiators may be used singly or in combination with various reductants such as amines, aldehydes, mercaptans and sulfinate salts. These reductants may be suitably used also in combination with the visible light photopolymerization initiators described hereinabove.

The polymerization initiators or the photopolymerization initiators may be used singly, or two or more may be used in appropriate combination. The amount thereof is usually in the range of 0.01 to 20 wt %, and preferably 0.1 to 5 wt % relative to the dental composition taken as 100 wt %.

The filler may be any of general fillers used in the dental field. The fillers are usually broadly categorized into organic fillers and inorganic fillers.

Examples of the organic fillers include fine powders of polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer and styrene-butadiene copolymer.

Examples of the inorganic fillers include fine powders of various glasses (based on silicon dioxide and optionally containing oxides of, for example, heavy metals, boron and aluminum), various ceramics, diatomaceous earth, kaolin, clay minerals (such as montmorillonite), activated clay, synthetic zeolite, mica, calcium fluoride, ytterbium fluoride, calcium phosphate, barium sulfate, zirconium dioxide, titanium dioxide and hydroxyapatite. Specific examples of the inorganic fillers include barium borosilicate glasses (such as Kimble Raysorb T3000, Schott 8235, Schott GM27884 and Schott GM39923), strontium boroaluminosilicate glasses (such as Raysorb T4000, Schott G018-093 and Schott GM32087), lanthanum glasses (such as Schott GM31684), fluoroaluminosilicate glasses (such as Schott G018-091 and Schott G018-117), and boroaluminosilicate glasses containing zirconium and/or cesium (such as Schott G018-307, G018-308 and G018-310).

In an embodiment, an organic inorganic composite filler may be used which is obtained by adding a polymerizable monomer beforehand to the inorganic filler to give a paste, which is then cured by polymerization and crushed.

In a preferred embodiment of the dental composition, the composition contains a microfiller having a particle diameter of 0.1 μm or less. Such a composition is suited as a dental composite resin. Preferred examples of the materials for such micron size fillers include silica (for example, product name: AEROSIL), alumina, zirconia and titania. The addition of such a micron size inorganic filler is advantageous in order for a cured product of the composite resin to achieve high polish and smoothness by being polished.

These fillers may have been surface treated with agents such as silane coupling agents in accordance with purposes.

Examples of such surface treating agents include known silane coupling agents, for example, organosilicon compounds such as γ-methacryloxyalkyltrimethoxysilanes (the number of carbon atoms between the methacryloxy group and the silicon atom: 3 to 12), γ-methacryloxyalkyltriethoxysilanes (the number of carbon atoms between the methacryloxy group and the silicon atom: 3 to 12), vinyltrimethoxysilane, vinylethoxysilane and vinyltriacetoxysilane. The surface treating agent is usually used with a concentration in the range of 0.1 to 20 wt %, and preferably 1 to 10 wt % with respect to 100 wt % of the filler.

The fillers may be used singly, or two or more may be used in combination appropriately. The amount of the filler may be determined appropriately in consideration of handling properties (viscosity) of the composite resin paste and mechanical properties of cured products of the paste. The amount is usually 10 to 2000 parts by weight, preferably 50 to 1000 parts by weight, and more preferably 100 to 600 parts by weight with respect to 100 parts by weight of all the components present in the dental composition except the filler.

The dental composition of the invention may contain components other than the inventive dental polymerizable monomer composition, the polymerization initiator and the filler appropriately in accordance with the purpose. For example, the composition may contain any of the polymerization inhibitors described hereinabove in order to exhibit enhanced storage stability. To control the color tone, known colorants such as pigments and dyes may be added. Further, known reinforcing materials such as fibers may be added to increase the strength of cured products.

The dental composition of the invention may be cured under appropriate conditions in accordance with the manner in which the polymerization initiator initiates the polymerization. In the case where, for example, the inventive dental composition contains a visible light photopolymerization initiator, a desired cured product may be obtained by shaping the dental composition into a prescribed form and irradiating the shape with visible light for a prescribed time using a known irradiator. The conditions such as intensity and dose may be controlled appropriately in accordance with the curability of the dental composition. The cured product that has been cured by the application of light such as visible light may be heat treated under appropriate conditions, and thereby the mechanical properties of the cured product can be enhanced.

The cured products from the inventive dental composition that are obtained as described above may be suitably used as dental materials.

The dental composition of the invention may be used by any known methods generally adopted for dental materials without limitation. When, for example, the inventive dental composition is used as a composite resin for filling carious cavities, the purpose may be fulfilled by filling a cavity in the mouth with the dental composition and photocuring the composition using a known irradiator. When used as a crowning composite resin, the composition may be shaped into an appropriate form, photocured with a known irradiator and heat treated under prescribed conditions to give a desired crown material.

The cured products that are obtained from the inventive dental composition including the inventive dental polymerizable monomer composition have high mechanical properties as compared to cured products from a conventional dental composition containing a conventional dental polymerizable monomer composition, and in particular exhibit high flexural breaking strength. The detailed reasons as to why the cured products of the inventive dental compositions have high mechanical properties are not fully understood. In the dental composition or in particular a composite resin as a typical example, the major proportion of the weight of the composition is accounted for by the polymerizable monomer composition and the filler, and therefore these two components have a very high influence on the mechanical properties of the composite resin cured products. In general, an inorganic filler has a far higher strength than a cured product of the dental polymerizable monomer composition. In contrast, the cured product of the inventive dental polymerizable monomer composition has excellent flexibility. Thus, in the composite resin cured product, the inorganic filler may be considered as a hard segment component and the cured product as a soft segment component. In such a system, blindly increasing the rigidity of the soft segment component does not lead to an enhancement in the mechanical properties of the composite resin cured product or rather often results in a hard but brittle material. As far as the soft segment component is concerned, it is probable that increasing the toughness thereof while maintaining a certain level of rigidity will contribute to enhancing the mechanical properties of the composite resin cured product. When cured, the dental polymerizable monomer composition of the invention gives a material having toughness and rigidity by virtue of its containing the specific amount of the urethane acrylate compound (A) with the specific structure. Such a cured product is suited as the soft segment component in the composite resin cured product, and has high mechanical properties and, in particular, will exhibit high flexural breaking strength.

The dental composition of the invention may be suitably used as a dental material. Examples of such materials include dental restorative materials, denture base resins, denture base liners, impression materials, dental luting materials (resin cements, resin glass ionomer cements), dental bonding materials (orthodontic bonding materials, cavity-coating bonding materials), dental fissure sealants, CAD/CAM resin blocks, temporary crowns and artificial tooth materials.

The dental composition of the invention may be suitably used also as a dental restorative material. The dental restorative materials are classified by application into categories such as dental crown composite resins, composite resins for filling carious cavities, composite resins for making dental abutments, and restorative composite resin fillers. By virtue of their high mechanical properties, the cured products of the inventive dental compositions are particularly suited for use as dental crown composite resins.

EXAMPLES

The present invention will be described in further detail based on Examples hereinbelow without limiting the scope of the invention to such Examples.

The following is the abbreviations of compounds used in Examples of the invention.
TEGDMA: triethylene glycol dimethacrylate
DEGDMA: diethylene glycol dimethacrylate
TEGDA: triethylene glycol diacrylate
EBADMA (4.0): ethoxylated bisphenol A dimethacrylate (4.0 EO modification)
UDMA: 2,2,4-trimethylhexamethylenebis(2-carbamoyloxyethyl) dimethacrylate
HEA: 2-hydroxyethyl acrylate
TMXDI: 1,3-tetramethylxylylene diisocyanate
DBTDL: dibutyltin dilaurate
BHT: dibutylhydroxytoluene
CQ: camphorquinone
DMAB2-BE: 2-butoxyethyl 4-(dimethylamino)benzoate

[Bending Test Method]

The bending test method used in Examples and Comparative Examples in the invention will be described below.

(Fabrication of Bending Test Pieces Including Dental Polymerizable Monomer Compositions)

0.5 Parts by weight of CQ and 0.5 parts by weight of DMAB2-BE were added to 100 parts by weight of a dental polymerizable monomer composition from any of Examples and Comparative Examples. The mixture was stirred to uniformity at room temperature to give a photopolymerizable monomer solution. The photopolymerizable monomer solution was added into a 2×2×25 mm stainless steel mold and was irradiated with light from a visible light irradiator (Solidilite V manufactured by SHOFU INC.) for 3 minutes on each side, namely, for a total of 6 minutes on both sides. The test piece was removed from the mold and was heat treated in an oven at 110° C. for 15 minutes. The test piece was removed from the oven and was cooled to room temperature. Thereafter, the test piece was soaked in distilled water in a closable sample bottle and was stored at 37° C. for 24 hours. The test piece thus obtained was subjected to testing.

(Fabrication of Bending Test Pieces Including Dental Compositions)

A photopolymerizable monomer solution was provided which included 100 parts by weight of a dental polymerizable monomer composition from any of Examples and Comparative Examples, 0.5 parts by weight of CQ and 0.5 parts by weight of DMAB2-BE. To the solution, 300 parts by weight of silica glass (Fuselex-X (TATSUMORI LTD.)) was added. The mixture was stirred to uniformity in a mortar and was degassed to give a dental polymerizable composition. The dental polymerizable composition obtained was added into a 2×2×25 mm stainless steel mold and was irradiated with light from a visible light irradiator (Solidilite V manufactured by SHOFU INC.) for 3 minutes on each side, namely, for a total of 6 minutes on both sides. The test piece was removed from the mold and was heat treated in an oven at 110° C. for 15 minutes. The test piece was removed from the oven and was cooled to room temperature. Thereafter, the test piece was soaked in distilled water in a closable sample bottle and was stored at 37° C. for 24 hours. The test piece thus obtained was subjected to testing.

(Bending Test)

The test pieces fabricated in the above manners were subjected to a three-point bending test with a tester (AUTOGRAPH EZ-S manufactured by Shimadzu Corporation) under conditions in which the distance between the supports was 20 mm and the cross head speed was 1 ram/min. In Table 2, the values in parenthesis in the sections of flexural breaking strength and fracture energy indicate increases or decreases in % relative to the values measured in Comparative Example 1.

[Viscosity Method]

In Examples and Comparative Examples of the invention, the viscosity was measured with a cone-plate viscometer (TVE-22H manufactured by TOKI SANGYO CO., LTD.). The temperature was controlled at 25° C. with use of a circulation thermostatic tank.

The viscosity in Production Examples of the invention was measured with the above cone-plate viscometer while controlling the temperature at 65° C. with use of a circulation thermostatic tank.

Production Example 1

A thoroughly dried 1-liter four-necked flask equipped with a stirring blade and a thermometer was loaded with 270.0 g (2.325 mol) of HEA, 0.55 g of DBTDL (0.1 wt % relative to the total weight of hydroxyethyl acrylate and TMXDI) and 0.28 g of BHT (0.05 wt % relative to the total weight of HEA and TMXDI). The mixture was stirred to uniformity and was thereafter heated to 60° C. Subsequently, 284.0 g (1.163 mol) of TMXDI was added dropwise over a period of 1 hour. The dropwise addition was accompanied by an increase in inside temperature due to the reaction heat, and thus the rate of the dropwise addition was controlled so that the temperature did not exceed 80° C. After the whole amount had been added dropwise, the reaction was performed for 10 hours while keeping the reaction temperature at 80° C. During this process, the progress of the reaction was tracked by HPLC analysis to determine the end point of the reaction. The product was discharged from the reactor. In this manner, 530 g of a urethane acrylate represented by the following formula was obtained. The viscosity at 65° C. was 1670 mPa·s.

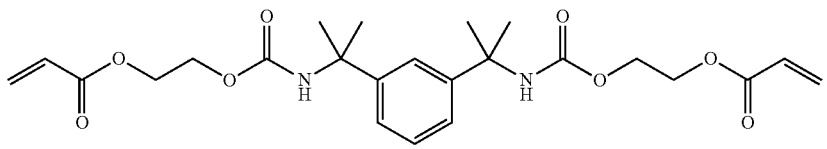 [SMILES: C=CC(=O)OCCOC(=O)NC(C)(C)c1cccc(C(C)(C)NC(=O)OCCOC(=O)C=C)c1]

Production Examples 2 to 8

Urethane acrylates were synthesized from hydroxyacrylates and diisocyanates illustrated in Table 1 in the same manner as in Production Example 1.

TABLE 1

| | Hydroxyacrylates | Diisocyanates |
|---|---|---|
| Pro. Ex. 1 | 2-hydroxyethyl acrylate | 1,3-bis(2-isocyanatopropan-2-yl)benzene |
| Pro. Ex. 2 | 2-hydroxypropyl acrylate | 1,3-bis(2-isocyanatopropan-2-yl)benzene |
| Pro. Ex. 3 | 4-hydroxybutyl acrylate | 1,3-bis(2-isocyanatopropan-2-yl)benzene |
| Pro. Ex. 4 | 2-hydroxyethyl acrylate and 4-hydroxybutyl acrylate, 1:3 Mixture of two compounds above (by mol) | 1,3-bis(2-isocyanatopropan-2-yl)benzene |
| Pro. Ex. 5 | 2-hydroxypropyl acrylate | 1,3-bis(isocyanatomethyl)benzene |
| Pro. Ex. 6 | 2-hydroxyethyl acrylate | bis(isocyanatomethyl)norbornane |
| Pro. Ex. 7 | 2-hydroxy-2-ethyl ethyl acrylate | 1,3-bis(2-isocyanatopropan-2-yl)benzene |
| Pro. Ex. 8 | 2-hydroxypropyl methacrylate | 1,3-bis(2-isocyanatopropan-2-yl)benzene |

| | Products | Viscosity (mPa · s (65° C.)) |
|---|---|---|
| Pro. Ex. 1 | diacrylate urethane product | 1670 |

TABLE 1-continued

| Pro. Ex. 2 | [structure] | 1800 |
| Pro. Ex. 3 | [structure] | 410 |
| Pro. Ex. 4 | [structure] | 700 |
| | [structure] | |
| | [structure] | |
| | Mixture of three compounds above | |
| Pro. Ex. 5 | [structure] | 570 |
| Pro. Ex. 6 | [structure] | 930 |
| Pro. Ex. 7 | [structure] | 1770 |
| Pro. Ex. 8 | [structure] | 1900 |

Example 1

10.0 g (21.3 mmol) of the urethane acrylate obtained in Production Example 1 and 4.53 g (15.8=1) of TEGDMA were added into a container. The mixture was stirred to uniformity at 50° C. to give a dental polymerizable monomer composition. In this case, the urethane acrylate from Production Example 1 had two acryloyl groups and TEGDMA had two methacryloyl groups. Thus, the proportion of the number of the acryloyl groups present in the urethane acrylate (A), namely, the urethane acrylate from Production Example 1 was 57% relative to the total number of the polymerizable groups in the dental polymerizable monomer composition, and the ratio of the acryloyl groups to the methacryloyl groups in the composition was 57:43.

73 mg (0.5 wt %) of CQ and 73 mg (0.5 wt %) of DMAB2-BE were added to 14.53 g of the dental polymerizable monomer composition, and the mixture was stirred to uniformity at room temperature to give a monomer solution. A cured product of the monomers was subjected to the bending test, which resulted in an elastic modulus of 3.4 GPa, a flexural breaking strength of 142 MPa, and a fracture energy of 62 mJ.

Examples 2 to 17

Dental polymerizable monomer compositions were obtained in the same manner as in Example 1 using the urethane acrylates and additional polymerizable monomers described in Table 2. The bending test was performed in the same manner as in Example 1, the results being described in Table 2.

Example 18

A dental composition in the form of a uniform paste was obtained by admixing 300 parts by weight of a filler (Fuselex-X), 0.5 parts by weight of CQ and 0.5 parts by weight of DMAB2-BE to 100 parts by weight of the dental polymerizable monomer composition obtained in Example 1. Table 3 describes the results of the bending test with respect to a cured product of the dental composition.

Examples 19 to 22

Dental compositions were obtained in the same manner except that the dental polymerizable monomer composition from Example 1 was replaced by any one of the dental polymerizable monomer compositions obtained in Examples 2, 3, 5 and 6. Table 3 describes the results of the bending test with respect to cured products of the dental compositions.

Comparative Example 1

A dental polymerizable monomer composition was obtained in the same manner as in Example 1 except that the urethane acrylate from Production Example 1 was replaced by the equimolar amount of UDMA. The bending test was performed in the same manner as in Example 1, the results being described in Table 2. While the composition of Comparative Example 1 did not contain any urethane acrylates (A), the amount in mol % indicated in parenthesis in the section of "Urethane acrylates (A)" in Table 2, and the proportion in % indicated in parenthesis in the section of "Proportion of number of acryloyl groups in urethane acrylate (A) to total number of polymerizable groups" are the amount in mol % of UDMA present in the composition and the proportion of the methacryloyl groups present in UDMA to the total number of the polymerizable groups, respectively.

Comparative Example 2

A dental polymerizable monomer composition was obtained in the same manner as in Example 1 except that the urethane acrylate from Production Example 1 was replaced by the equimolar amount of the urethane methacrylate obtained in Production Example 8. The bending test was performed in the same manner as in Example 1, the results being described in Table 2. While the composition of Comparative Example 2 did not contain any urethane acrylates (A), the amount in mol % indicated in parenthesis in the section of "Urethane acrylates (A)" in Table 2, and the proportion in % indicated in parenthesis in the section of "Proportion of number of acryloyl groups in urethane acrylate (A) to total number of polymerizable groups" are the amount in mol % of the urethane methacrylate from Production Example 8 in the composition and the proportion of the methacryloyl groups present in the methacrylate from Production Example 8 to the total number of the polymerizable groups, respectively.

Comparative Example 3

The procedures in Example 1 were repeated except that TEGDMA alone was used as the dental polymerizable monomer composition. The results of the bending test are described in Table 2.

Comparative Example 4

The procedures in Example 1 were repeated except that TEGDA alone was used as the dental polymerizable monomer composition. The results of the bending test are described in Table 2.

Comparative Example 5

A dental composition in the form of a uniform paste was obtained in the same manner as in Example 18 except that the dental polymerizable monomer composition from Comparative Example 1 was used. Table 3 describes the results of the bending test with respect to a cured product of the dental composition.

Comparative Example 6

A dental composition in the form of a uniform paste was obtained in the same manner as in Example 18 except that the dental polymerizable monomer composition from Comparative Example 2 was used. Table 3 describes the results of the bending test with respect to a cured product of the dental composition.

TABLE 2

| | Urethane acrylates (A) | Additional polymerizable monomers (B) | Proportion of number of acryloyl groups in urethane acrylate (A) to total number of polymerizable groups | Ratio of acryloyl groups to methacryloyl groups in composition | Viscosity of polymerizable monomer composition (mPa · s (25° C.)) | Results of bending test with respect to cured products of polymerizable monomer compositions | | |
|---|---|---|---|---|---|---|---|---|
| | | | | | | Elastic modulus (GPa) | Flexural breaking strength (MPa) | Fracture energy (mJ) |
| Ex. 1 | Pro. Ex. 1/57 mol % | TEGDMA/43 mol % | 57% | 57:43 | 1800 | 3.4 | 142 (+38%) | 62 (+44%) |
| Ex. 2 | Pro. Ex. 2/57 mol % | TEGDMA/43 mol % | 57% | 57:43 | 1940 | 3.3 | 135 (+31%) | 58 (+35%) |
| Ex. 3 | Pro. Ex. 3/57 mol % | TEGDMA/43 mol % | 57% | 57:43 | 820 | 2.5 | 111 (+8%) | 111 (+158%) |

TABLE 2-continued

| | Urethane acrylates (A) | Additional polymerizable monomers (B) | Proportion of number of acryloyl groups in urethane acrylate (A) to total number of polymerizable groups | Ratio of acryloyl groups to methacryloyl groups in composition | Viscosity of polymerizable monomer composition (mPa·s (25° C.)) | Results of bending test with respect to cured products of polymerizable monomer compositions | | |
|---|---|---|---|---|---|---|---|---|
| | | | | | | Elastic modulus (GPa) | Flexural breaking strength (MPa) | Fracture energy (mJ) |
| Ex. 4 | Pro. Ex. 4/57 mol % | TEGDMA/43 mol % | 57% | 57:43 | 1060 | 2.9 | 122 (+18%) | 79 (+84%) |
| Ex. 5 | Pro. Ex. 5/57 mol % | TEGDMA/43 mol % | 57% | 57:43 | 560 | 3.2 | 136 (+32%) | 63 (+47%) |
| Ex. 6 | Pro. Ex. 6/57 mol % | TEGDMA/43 mol % | 57% | 57:43 | 910 | 2.6 | 129 (+25%) | 66 (+53%) |
| Ex. 7 | Pro. Ex. 7/57 mol % | TEGDMA/43 mol % | 57% | 57:43 | 1940 | 2.8 | 120 (+17%) | 54 (+26%) |
| Ex. 8 | Pro. Ex. 1/53 mol % | TEGDMA/47 mol % | 53% | 53:47 | 860 | 3.2 | 137 (+33%) | 64 (+49%) |
| Ex. 9 | Pro. Ex. 1/64 mol % | TEGDMA/36 mol % | 64% | 64:36 | 3500 | 3.5 | 146 (+42%) | 72 (+67%) |
| Ex. 10 | Pro. Ex. 1/71 mol % | TEGDMA/29 mol % | 71% | 71:29 | 12250 | 3.5 | 151 (+47%) | 75 (+74%) |
| Ex. 11 | Pro. Ex. 1/54 mol % | DEGDMA/46 mol % | 54% | 54:46 | 1320 | 3.6 | 151 (+47%) | 63 (+47%) |
| Ex. 12 | Pro. Ex. 1/67 mol % | DEGDMA/33 mol % | 67% | 67:33 | 10260 | 3.6 | 155 (+50%) | 68 (+58%) |
| Ex. 13 | Pro. Ex. 5/62 mol % | DEGDMA/38 mol % | 62% | 62:38 | 1050 | 3.4 | 151 (+47%) | 66 (+53%) |
| Ex. 14 | Pro. Ex. 6/62 mol % | DEGDMA/38 mol % | 62% | 62:38 | 2000 | 2.9 | 138 (+34%) | 71 (+65%) |
| Ex. 15 | Pro. Ex. 1/73 mol % | EBADMA/27 mol % | 73% | 73:27 | 50000 | 3.2 | 130 (+26%) | 81 (+88%) |
| Ex. 16 | Pro. Ex. 1/64 mol % | TEGDMA/18 mol % TEGDA/18 mol % | 64% | 82:18 | 4300 | 3.2 | 129 (+25%) | 73 (+70%) |
| Ex. 17 | Pro. Ex. 1/15 mol % | UDMA/42 mol % TEGDMA/43 mol % | 15% | 15:85 | 400 | 2.6 | 120 (+17%) | 53 (+23%) |
| Comp. Ex. 1 | (UDMA/57 mol %)*1 | TEGDMA/43 mol % | (57%)*2 | 0:100 | 340 | 2.3 | 103 | 43 |
| Comp. Ex. 2 | (Pro. Ex. 8/57 mol %)*3 | TEGDMA/43 mol % | (57%)*4 | 0:100 | 2310 | 3.4 | 135 (+31%) | 44 (+2%) |
| Comp. Ex. 3 | — | TEGDMA/100 mol % | 0% | 0:100 | 9 | 1.7 | 60 (−42%) | 14 (−67%) |
| Comp. Ex. 4 | — | TEGDA/100 mol % | 0% | 100:0 | 13 | 0.8 | 28 (−73%) | 14 (−67%) |

The values in parenthesis in the sections of flexural breaking strength and fracture energy indicate Increases or decreases in % relative to the values measured in Comparative Example 1.
*1 The amount in mol % of UDMA present in the composition.
*2 The proportion of the number of the methacryloyl groups in UDMA to the total number of the polymerizable groups.
*3 The amount in mol % of the methacrylate from Production Example 8 in the composition.
*4 The proportion of the number of the methacryloyl groups in the methacrylate from Production Example 8 to the total number of the polymerizable groups.

TABLE 3

| | Dental polymerizable monomer compositions | Flexural elastic modulus (GPa) | Flexural breaking strength (MPa) |
|---|---|---|---|
| Ex. 18 | Ex. 1 | 15.9 | 201 |
| Ex. 19 | Ex. 2 | 15.7 | 208 |
| Ex. 20 | Ex. 3 | 14.5 | 185 |
| Ex. 21 | Ex. 5 | 15.7 | 217 |
| Ex. 22 | Ex. 6 | 14.8 | 217 |
| Comp. Ex. 5 | Comp. Ex. 1 | 15.7 | 156 |
| Comp. Ex. 6 | Comp. Ex. 2 | 14.8 | 176 |

The results in Table 2 have shown that the cured products of the inventive dental polymerizable monomer compositions compared equally or favorably in flexural breaking strength to the cured products of the conventional dental polymerizable monomer compositions, and at the same time achieved a significant enhancement in fracture energy. That is, the cured products of the inventive dental polymerizable monomer compositions have been demonstrated to be materials exhibiting both toughness and rigidity.

Further, the results in Table 3 have shown that the cured products from the dental compositions containing the inventive dental polymerizable monomer compositions achieved a marked enhancement in flexural breaking strength as compared to the cured products of the conventional dental compositions. Thus, it has been demonstrated that the incorporation of the inventive dental polymerizable monomer compositions having both toughness and rigidity enhances the flexural breaking strength of the cured products of the dental compositions.

The invention claimed is:

1. A dental polymerizable monomer composition comprising a urethane acrylate compound (A) and a polymerizable compound (B) having at least one polymerizable group selected from methacryloyl groups and acryloyl groups, the dental polymerizable monomer composition satisfying (I) and (II) below:
   (I) the urethane acrylate compound (A) is obtained by reacting a hydroxyacrylate (a1) represented by the general formula (1) below with a diisocyanate (a2) having two isocyanate groups bonded to a divalent $C_{6-9}$ aromatic hydrocarbon group or a divalent $C_{6-9}$ bridged cyclic hydrocarbon group via a methylene group optionally substituted with a hydrocarbon group;
   (II) the proportion of the number of acryloyl groups present in the urethane acrylate compound (A) is 10% to less than 90% relative to the total number of methacryloyl groups and acryloyl groups in the polymerizable monomer composition;

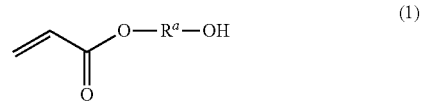

(in the general formula (1), $R^a$ represents a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom).

2. The dental polymerizable monomer composition according to claim 1, wherein the proportion of the number of acryloyl groups present in the urethane acrylate compound (A) is 40% to less than 90% relative to the total number of methacryloyl groups and acryloyl groups in the polymerizable monomer composition.

3. The dental polymerizable monomer composition according to claim 1, wherein the ratio of the acryloyl groups to the methacryloyl groups present in the dental polymerizable monomer composition is in the range of 10:90 to 90:10.

4. The dental polymerizable monomer composition according to claim 1, wherein the ratio of the acryloyl groups to the methacryloyl groups present in the dental polymerizable monomer composition is in the range of 40:60 to 90:10.

5. The dental polymerizable monomer composition according to claim 1, wherein the diisocyanate (a2) is at least one selected from compounds represented by the general formula (2) below:

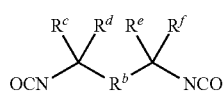
(2)

(in the general formula (2), $R^b$ represents a divalent $C_{6-9}$ aromatic hydrocarbon group or a divalent $C_{6-9}$ bridged cyclic hydrocarbon group; and $R^c$, $R^d$, $R^e$ and $R^f$ are each hydrogen or a methyl group).

6. The dental polymerizable monomer composition according to claim 5, wherein the diisocyanate (a2) is at least one selected from compounds represented by the general formulas (3) to (5) below:

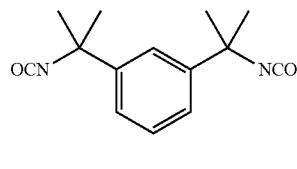
(3)

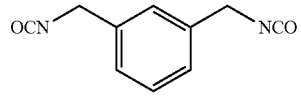
(4)

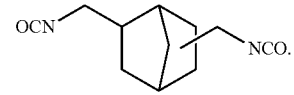
(5)

7. The dental polymerizable monomer composition according to claim 6, wherein the urethane acrylate (A) is at least one compound represented by the general formula (6) below:

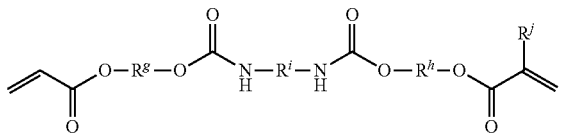
(6)

(in the general formula (6), $R^i$ is a group represented by the formula (7), (8) or (9) below; $R^g$ and $R^h$ are each independently a $C_{2-6}$ linear alkylene group or a $C_{2-6}$ linear oxyalkylene group, each of which is optionally substituted with a $C_{1-3}$ alkyl group or a (meth)acryloyloxymethylene group in place of a hydrogen atom; and $R^j$ represents a hydrogen atom or a methyl group);

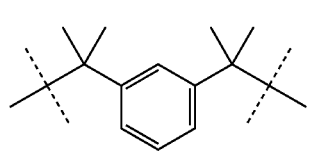
(7)

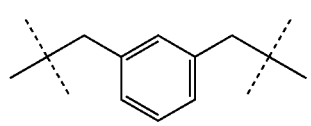
(8)

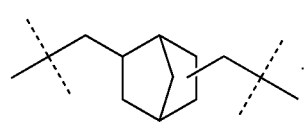
(9)

8. The dental polymerizable monomer composition according to claim 1, wherein $R^a$ in the general formula (1) independently at each occurrence represents a $C_{2-6}$ linear alkylene group or a $C_{2-6}$ linear oxyalkylene group, each of which is optionally substituted with a $C_{1-3}$ alkyl group in place of a hydrogen atom.

9. The dental polymerizable monomer composition according to claim 7, wherein $R^g$ and $R^h$ in the general formula (6) are each independently a $C_{2-6}$ linear alkylene group or a $C_{2-6}$ linear oxyalkylene group, each of which is optionally substituted with a $C_{1-3}$ alkyl group in place of a hydrogen atom, and $R^j$ is a hydrogen atom.

10. The dental polymerizable monomer composition according to claim 1, wherein the viscosity at 25° C. is 1 to 100,000 mPa·s.

11. A dental composition comprising the dental polymerizable monomer composition described in claim 1, a polymerization initiator and a filler.

12. A dental material obtained by curing the dental composition described in claim 11.

* * * * *